(12) United States Patent
Burnett et al.

(10) Patent No.: US 8,435,166 B2
(45) Date of Patent: May 7, 2013

(54) METHOD AND APPARATUS FOR MAGNETIC INDUCTION THERAPY

(75) Inventors: Daniel Rogers Burnett, San Francisco, CA (US); Christopher Hermanson, Santa Cruz, CA (US)

(73) Assignee: EMKinetics, Inc., Mountain View, CA (US)

( * ) Notice: Subject to any disclaimer, the term of this patent is extended or adjusted under 35 U.S.C. 154(b) by 402 days.

(21) Appl. No.: 12/469,358

(22) Filed: May 20, 2009

(65) Prior Publication Data
US 2009/0234179 A1     Sep. 17, 2009

Related U.S. Application Data

(63) Continuation of application No. 11/866,329, filed on Oct. 2, 2007.

(60) Provisional application No. 60/848,720, filed on Oct. 2, 2006.

(51) Int. Cl.
*A61N 2/04*     (2006.01)

(52) U.S. Cl.
USPC .............................................. 600/13

(58) Field of Classification Search .......... 600/9–15
See application file for complete search history.

(56) References Cited

U.S. PATENT DOCUMENTS

| | | |
|---|---|---|
| 2,893,392 A | 7/1959 | Wagner et al. |
| 3,034,507 A | 5/1962 | McConnell et al. |
| 3,817,254 A | 6/1974 | Maurer |
| 3,841,305 A | 10/1974 | Hallgren |
| 4,266,533 A | 5/1981 | Ryaby et al. |
| 4,428,366 A | 1/1984 | Findl et al. |
| 4,456,012 A | 6/1984 | Lattin |
| 4,548,208 A | 10/1985 | Niemi |
| 4,574,809 A | 3/1986 | Talish et al. |

(Continued)

FOREIGN PATENT DOCUMENTS

| | | |
|---|---|---|
| GB | 0637560 | 5/1950 |
| GB | 2298370 | 9/1996 |

(Continued)

OTHER PUBLICATIONS

"Bioflex® RX754P, Single Coated Medical Pressure Sensitive Adhesive Tape," *Technical Data*, 2 pages, Dec. 2005.

(Continued)

*Primary Examiner* — Charles A Marmor, II
*Assistant Examiner* — Catherine E Burk
(74) *Attorney, Agent, or Firm* — Levine Bagade Han LLP

(57) ABSTRACT

An energy emitting apparatus for providing a medical therapy includes one or more energy generators, a logic controller electrically connected to the one or more energy generators, and one or more sensors for detecting electric conduction in a target nerve that are connected to the logic controller. The one or more energy generators produce energy focused on the target nerve upon receiving a signal from the logic controller, and the energy is varied by the logic controller according to an input provided by the one or more sensors. In one embodiment, the energy emitting apparatus is an apparatus for magnetic induction therapy that includes one or more conductive coils disposed in an ergonomic housing that produce a magnetic field focused on the target nerve upon receiving an electric current from the logic controller based on an input provided by the one or more sensors.

15 Claims, 8 Drawing Sheets

U.S. PATENT DOCUMENTS

| | | | |
|---|---|---|---|
| 4,784,737 A | 11/1988 | Ray et al. | |
| 4,804,054 A | 2/1989 | Howson et al. | |
| 4,915,110 A | 4/1990 | Kitov | |
| 4,926,878 A | 5/1990 | Snedeker | |
| 4,940,453 A * | 7/1990 | Cadwell | 600/13 |
| 5,000,178 A | 3/1991 | Griffith | |
| 5,014,699 A | 5/1991 | Pollack et al. | |
| 5,181,902 A | 1/1993 | Erickson et al. | |
| 5,309,909 A | 5/1994 | Gadsby et al. | |
| 5,314,401 A | 5/1994 | Tepper | |
| 5,314,453 A | 5/1994 | Jeutter | |
| 5,401,233 A | 3/1995 | Erickson et al. | |
| 5,449,378 A | 9/1995 | Schouenborg | |
| 5,518,495 A | 5/1996 | Kolt | |
| 5,562,707 A | 10/1996 | Prochazka et al. | |
| 5,690,693 A | 11/1997 | Wang et al. | |
| 5,715,837 A | 2/1998 | Chen | |
| 5,725,471 A | 3/1998 | Davey et al. | |
| 5,749,909 A | 5/1998 | Schroeppel et al. | |
| 5,766,124 A | 6/1998 | Polson | |
| 5,792,187 A | 8/1998 | Adams | |
| 5,792,209 A | 8/1998 | Varner | |
| 5,833,600 A | 11/1998 | Young | |
| 5,857,957 A | 1/1999 | Lin | |
| 5,978,712 A | 11/1999 | Suda et al. | |
| 5,984,854 A * | 11/1999 | Ishikawa et al. | 600/9 |
| 6,009,878 A | 1/2000 | Weijand et al. | |
| 6,024,691 A | 2/2000 | Tepper et al. | |
| 6,029,090 A | 2/2000 | Herbst | |
| 6,032,677 A | 3/2000 | Blechman et al. | |
| 6,066,084 A | 5/2000 | Edrich et al. | |
| 6,086,525 A | 7/2000 | Davey et al. | |
| 6,088,619 A | 7/2000 | Hein et al. | |
| 6,123,658 A | 9/2000 | Schweighofer et al. | |
| 6,143,035 A | 11/2000 | McDowell | |
| 6,155,966 A | 12/2000 | Parker | |
| 6,179,770 B1 | 1/2001 | Mould | |
| 6,190,893 B1 | 2/2001 | Shastri et al. | |
| 6,200,259 B1 | 3/2001 | March | |
| 6,213,933 B1 | 4/2001 | Lin | |
| 6,219,575 B1 | 4/2001 | Nemati | |
| 6,256,533 B1 | 7/2001 | Yuzhakov et al. | |
| 6,261,221 B1 | 7/2001 | Tepper et al. | |
| 6,312,612 B1 | 11/2001 | Sherman et al. | |
| 6,334,856 B1 | 1/2002 | Allen et al. | |
| 6,349,233 B1 | 2/2002 | Adams | |
| 6,366,795 B1 | 4/2002 | Bremer et al. | |
| 6,379,324 B1 | 4/2002 | Gartstein et al. | |
| 6,440,096 B1 | 8/2002 | Lastovich et al. | |
| 6,443,883 B1 | 9/2002 | Ostrow et al. | |
| 6,451,240 B1 | 9/2002 | Sherman et al. | |
| 6,471,903 B2 | 10/2002 | Sherman et al. | |
| 6,473,652 B1 | 10/2002 | Sarwal et al. | |
| 6,491,620 B1 | 12/2002 | Davey | |
| 6,493,588 B1 | 12/2002 | Malaney et al. | |
| 6,500,110 B1 | 12/2002 | Davey et al. | |
| 6,503,231 B1 | 1/2003 | Prausnitz et al. | |
| 6,511,463 B1 | 1/2003 | Wood et al. | |
| 6,527,694 B1 | 3/2003 | Ishikawa et al. | |
| 6,533,949 B1 | 3/2003 | Yeshurun et al. | |
| 6,537,242 B1 | 3/2003 | Palmer | |
| 6,553,263 B1 | 4/2003 | Meadows et al. | |
| 6,558,361 B1 | 5/2003 | Yeshurun | |
| 6,565,532 B1 | 5/2003 | Yuzhakov et al. | |
| 6,582,393 B2 | 6/2003 | Sage, Jr. | |
| 6,591,124 B2 | 7/2003 | Sherman et al. | |
| 6,595,947 B1 | 7/2003 | Mikszta et al. | |
| 6,603,987 B2 | 8/2003 | Whitson | |
| 6,611,707 B1 | 8/2003 | Prausnitz et al. | |
| 6,623,457 B1 | 9/2003 | Rosenberg | |
| 6,652,478 B1 | 11/2003 | Gartstein et al. | |
| 6,654,636 B1 | 11/2003 | Dev et al. | |
| 6,656,147 B1 | 12/2003 | Gertsek et al. | |
| 6,663,556 B2 | 12/2003 | Barker | |
| 6,663,820 B2 | 12/2003 | Arias et al. | |
| 6,671,527 B2 | 12/2003 | Petersson et al. | |
| 6,678,556 B1 | 1/2004 | Nolan et al. | |
| 6,689,100 B2 | 2/2004 | Connelly et al. | |
| 6,690,959 B2 | 2/2004 | Thompson | |
| 6,697,669 B2 | 2/2004 | Dev et al. | |
| 6,701,185 B2 | 3/2004 | Burnett et al. | |
| 6,735,474 B1 | 5/2004 | Loeb et al. | |
| 6,743,211 B1 | 6/2004 | Prausnitz et al. | |
| 6,767,341 B2 | 7/2004 | Cho | |
| 6,770,480 B1 | 8/2004 | Canham | |
| 6,790,372 B2 | 9/2004 | Roy et al. | |
| 6,808,506 B2 | 10/2004 | Lastovich et al. | |
| 6,835,184 B1 | 12/2004 | Sage et al. | |
| 6,866,659 B2 | 3/2005 | Nemati | |
| 6,881,203 B2 | 4/2005 | Delmore et al. | |
| 6,899,838 B2 | 5/2005 | Lastovich | |
| 6,908,453 B2 | 6/2005 | Fleming et al. | |
| 6,926,660 B2 | 8/2005 | Miller | |
| 6,931,277 B1 | 8/2005 | Yuzhakov et al. | |
| 6,939,311 B2 | 9/2005 | Geiger | |
| 6,941,171 B2 | 9/2005 | Mann et al. | |
| 6,960,193 B2 | 11/2005 | Rosenberg | |
| 6,962,772 B2 | 11/2005 | Liu et al. | |
| 6,972,013 B1 | 12/2005 | Zhang et al. | |
| 6,980,855 B2 | 12/2005 | Cho | |
| 7,013,179 B2 | 3/2006 | Carter et al. | |
| 7,027,478 B2 | 4/2006 | Ackley | |
| 7,032,302 B1 | 4/2006 | Schmidt et al. | |
| 7,045,069 B2 | 5/2006 | Ozeryansky | |
| 7,047,070 B2 | 5/2006 | Wilkinson et al. | |
| 7,048,723 B1 | 5/2006 | Frazier et al. | |
| 7,079,355 B2 | 7/2006 | Hsiao et al. | |
| 7,083,592 B2 | 8/2006 | Lastovich et al. | |
| 7,104,947 B2 | 9/2006 | Riehl | |
| 7,115,108 B2 | 10/2006 | Wilkinson et al. | |
| 7,117,034 B2 | 10/2006 | Kronberg | |
| 7,130,696 B2 | 10/2006 | Carter et al. | |
| 7,132,054 B1 | 11/2006 | Kravitz et al. | |
| 7,153,256 B2 | 12/2006 | Riehl et al. | |
| 7,187,976 B2 * | 3/2007 | Duncan et al. | 607/43 |
| 7,226,439 B2 | 6/2007 | Prausnitz et al. | |
| 7,262,068 B2 | 8/2007 | Roy et al. | |
| 7,273,474 B2 | 9/2007 | Chang et al. | |
| 7,285,113 B2 | 10/2007 | Yeshurun | |
| 7,315,758 B2 | 1/2008 | Kwiatkowski et al. | |
| 7,316,665 B2 | 1/2008 | Laurent et al. | |
| 7,320,664 B2 | 1/2008 | Riehl et al. | |
| 7,332,197 B2 | 2/2008 | Wood et al. | |
| 7,332,339 B2 | 2/2008 | Canham | |
| 7,344,499 B1 | 3/2008 | Prausnitz et al. | |
| 7,367,936 B2 | 5/2008 | Myers et al. | |
| D571,920 S | 6/2008 | Juliana et al. | |
| 7,396,326 B2 | 7/2008 | Ghiron et al. | |
| 7,410,476 B2 | 8/2008 | Wilkinson et al. | |
| 7,415,299 B2 | 8/2008 | Zimmermann et al. | |
| 7,416,541 B2 | 8/2008 | Yuzhakov et al. | |
| 7,429,333 B2 | 9/2008 | Chiou et al. | |
| 7,473,244 B2 | 1/2009 | Frazier et al. | |
| 7,481,337 B2 | 1/2009 | Luharuka et al. | |
| 7,497,980 B2 | 3/2009 | Xu et al. | |
| 7,500,911 B2 | 3/2009 | Johnson et al. | |
| 7,530,968 B2 | 5/2009 | Gonnelli | |
| 7,556,615 B2 | 7/2009 | Pettis et al. | |
| 7,556,821 B2 | 7/2009 | Ameri et al. | |
| 7,560,036 B2 | 7/2009 | Golubovic-Liakopoulos et al. | |
| 7,570,992 B2 | 8/2009 | Nolan et al. | |
| 7,572,405 B2 | 8/2009 | Sherman et al. | |
| 7,574,256 B2 | 8/2009 | Carter | |
| 7,578,954 B2 | 8/2009 | Gartstein et al. | |
| 7,582,069 B2 | 9/2009 | Laurent et al. | |
| 7,588,552 B2 | 9/2009 | Yeshurun et al. | |
| 7,591,806 B2 | 9/2009 | Xu | |
| 7,627,938 B2 | 12/2009 | Kim et al. | |
| 7,647,112 B2 | 1/2010 | Tracey et al. | |
| 7,648,484 B2 | 1/2010 | Yeshurun et al. | |
| 7,651,946 B2 | 1/2010 | Wilke et al. | |
| 7,658,728 B2 | 2/2010 | Yuzhakov | |
| 2002/0082465 A1 | 6/2002 | Bashford et al. | |
| 2002/0099323 A1 | 7/2002 | Dev et al. | |
| 2002/0111777 A1 | 8/2002 | David | |
| 2002/0133129 A1 | 9/2002 | Arias et al. | |
| 2003/0028072 A1 | 2/2003 | Fischell et al. | |

| | | | | | | |
|---|---|---|---|---|---|---|
| 2003/0144625 A1* | 7/2003 | Sherman et al. ............... 604/20 | | 2010/0204538 A1 | 8/2010 | Burnett et al. |
| 2003/0158583 A1 | 8/2003 | Burnett et al. | | 2010/0222629 A1 | 9/2010 | Burnett et al. |
| 2003/0158585 A1* | 8/2003 | Burnett ............... 607/2 | | 2010/0222630 A1 | 9/2010 | Mangrum et al. |
| 2003/0216729 A1 | 11/2003 | Marchitto et al. | | 2011/0021863 A1 | 1/2011 | Burnett et al. |
| 2004/0010276 A1 | 1/2004 | Jacobs et al. | | 2011/0295100 A1 | 12/2011 | Hedge et al. |
| 2004/0092860 A1 | 5/2004 | Dev et al. | | | | |
| 2004/0111139 A1 | 6/2004 | McCreery | | | | |
| 2004/0122787 A1 | 6/2004 | Avinash et al. | | | | |
| 2004/0138517 A1 | 7/2004 | Osorio et al. | | | | |
| 2004/0146611 A1 | 7/2004 | Arias et al. | | | | |
| 2004/0147964 A1 | 7/2004 | Nolan et al. | | | | |
| 2004/0173220 A1 | 9/2004 | Harry et al. | | | | |
| 2004/0210254 A1 | 10/2004 | Burnett et al. | | | | |
| 2004/0210282 A1 | 10/2004 | Flock et al. | | | | |
| 2005/0021104 A1 | 1/2005 | Dilorenzo | | | | |
| 2005/0029223 A1 | 2/2005 | Yeshurun | | | | |
| 2005/0099290 A1 | 5/2005 | Govari | | | | |
| 2005/0143783 A1 | 6/2005 | Boveja et al. | | | | |
| 2005/0143789 A1 | 6/2005 | Whitehurst et al. | | | | |
| 2005/0171576 A1 | 8/2005 | Williams et al. | | | | |
| 2005/0203602 A1 | 9/2005 | Wallace et al. | | | | |
| 2005/0277998 A1 | 12/2005 | Tracey et al. | | | | |
| 2005/0283202 A1 | 12/2005 | Gellman | | | | |
| 2006/0004244 A1 | 1/2006 | Phillips et al. | | | | |
| 2006/0016452 A1 | 1/2006 | Goetz et al. | | | | |
| 2006/0052839 A1 | 3/2006 | Kim et al. | | | | |
| 2006/0084938 A1 | 4/2006 | Zhang et al. | | | | |
| 2006/0122454 A1 | 6/2006 | Riehl et al. | | | | |
| 2006/0122660 A1 | 6/2006 | Boveja et al. | | | | |
| 2006/0135844 A1 | 6/2006 | Alekseyenko | | | | |
| 2006/0161039 A1 | 7/2006 | Juliana et al. | | | | |
| 2006/0199159 A1 | 9/2006 | Ghiron et al. | | | | |
| 2006/0276702 A1* | 12/2006 | McGinnis ............... 600/372 | | | | |
| 2007/0021803 A1 | 1/2007 | Deem et al. | | | | |
| 2007/0027353 A1 | 2/2007 | Ghiron et al. | | | | |
| 2007/0027354 A1 | 2/2007 | Riehl et al. | | | | |
| 2007/0027355 A1 | 2/2007 | Riehl et al. | | | | |
| 2007/0142885 A1 | 6/2007 | Hantash et al. | | | | |
| 2007/0208212 A1 | 9/2007 | Dilorenzo | | | | |
| 2007/0250162 A1 | 10/2007 | Royalty | | | | |
| 2007/0265489 A1* | 11/2007 | Fowler et al. ............... 600/12 | | | | |
| 2007/0276318 A1 | 11/2007 | Henley | | | | |
| 2007/0282246 A1 | 12/2007 | Henley | | | | |
| 2008/0004484 A1 | 1/2008 | Wieraszko et al. | | | | |
| 2008/0063866 A1 | 3/2008 | Allen et al. | | | | |
| 2008/0114199 A1 | 5/2008 | Riehl et al. | | | | |
| 2008/0177128 A1 | 7/2008 | Riehl et al. | | | | |
| 2008/0183070 A1 | 7/2008 | Unal et al. | | | | |
| 2008/0200748 A1 | 8/2008 | Testani et al. | | | | |
| 2008/0224808 A1 | 9/2008 | Ghiron et al. | | | | |
| 2008/0262287 A1 | 10/2008 | Dussau | | | | |
| 2008/0306325 A1 | 12/2008 | Burnett et al. | | | | |
| 2008/0312725 A1 | 12/2008 | Penner | | | | |
| 2009/0073991 A1 | 3/2009 | Landrum et al. | | | | |
| 2009/0076336 A1 | 3/2009 | Mazar et al. | | | | |
| 2009/0076340 A1 | 3/2009 | Libbus et al. | | | | |
| 2009/0076344 A1 | 3/2009 | Libbus et al. | | | | |
| 2009/0076345 A1 | 3/2009 | Manicka et al. | | | | |
| 2009/0076363 A1 | 3/2009 | Bly et al. | | | | |
| 2009/0076364 A1 | 3/2009 | Libbus et al. | | | | |
| 2009/0076397 A1 | 3/2009 | Libbus et al. | | | | |
| 2009/0076410 A1 | 3/2009 | Libbus et al. | | | | |
| 2009/0076559 A1 | 3/2009 | Libbus et al. | | | | |
| 2009/0076565 A1 | 3/2009 | Surwit | | | | |
| 2009/0118777 A1 | 5/2009 | Iki et al. | | | | |
| 2009/0132018 A1 | 5/2009 | DiUbaldi et al. | | | | |
| 2009/0162570 A1 | 6/2009 | Swenberg et al. | | | | |
| 2009/0171236 A1 | 7/2009 | Davies | | | | |
| 2009/0227829 A1 | 9/2009 | Burnett et al. | | | | |
| 2009/0227831 A1 | 9/2009 | Burnett et al. | | | | |
| 2009/0234410 A1 | 9/2009 | Libbus et al. | | | | |
| 2009/0264792 A1 | 10/2009 | Mazar | | | | |
| 2009/0292194 A1 | 11/2009 | Libbus et al. | | | | |
| 2010/0022864 A1 | 1/2010 | Cordero et al. | | | | |
| 2010/0049021 A1 | 2/2010 | Jina et al. | | | | |
| 2010/0056881 A1 | 3/2010 | Libbus et al. | | | | |
| 2010/0160712 A1 | 6/2010 | Burnett et al. | | | | |
| 2010/0161005 A1 | 6/2010 | Wahlgren et al. | | | | |
| 2010/0168501 A1 | 7/2010 | Burnett et al. | | | | |

FOREIGN PATENT DOCUMENTS

| | | |
|---|---|---|
| GB | 2336544 | 10/1999 |
| WO | WO 03/070317 | 8/2003 |
| WO | WO 2008/032279 | 3/2008 |
| WO | WO 2008/042902 | 4/2008 |
| WO | WO 2008/115426 | 9/2008 |
| WO | WO 2011/011748 | 1/2011 |
| WO | WO 2011/011749 | 1/2011 |
| WO | WO 2011/053607 | 5/2011 |
| WO | WO 2011/053661 | 5/2011 |

OTHER PUBLICATIONS

3M Corporation, 3M™ XYZ/Isotropic Electrically Conductive Adhesive Transfer Tape 9707, *3M Electronics Markets Materials Division*, 60-5002-0350-4, 8 pages, 2004, 3M.

Aaron, Roy K. et al., "Therapeutic Effects of Electromagnetic Fields in the Stimulation of Connective Tissue Repair," *Journal of Cellular Biography*, 52(1):42-6, May 1993, Wiley-Liss, Inc.

AmGel Technologies, "AG603 Sensing Gel, Sensing Gel. Designed for ECG Applications," AG603-3/10, 1 page, 2010.

AmGel Technologies, "AG702 Stimulating Gel, Stimulating Gel Designed for carbon film," AG702-02/06, 1 page, 2006.

AmGel Technologies, "AG902-184/229 Grounding Gel, Grounding Gel Designed for Electrosurgical Pads," AG902 Series, 1 page, 2010.

AmGel Technologies, "Release Films," 1 Page, Jul. 25, 2006, Revision 1.

Australian Patent Application No. 2007303223 filed Oct. 2, 2007 in the name of EMKinetics, Inc., Office Action mailed Sep. 7, 2010.

Balmaseda, Marion T. Jr., et al., "Burns in Functional Electric Stimulation: Two Case Reports," *Archives of Physical Medicine and Rehabilitation*, vol. 38., pp. 452-453, Jul. 1987.

Biowave Corporation, "510(k) Summary for the Biowave Deepwave Neuromodulation Pain Therapy Device," 6 pages, Appendix B, Dec. 13, 2005.

Biowave Corporation, "510(k) Summary for the Biowave Deepwave Neuromodulation Pain Therapy Device," 7 pages, Appendix E, Aug. 15, 2006.

Biowave Corporation, "Percutaneous Neuromodulation Pain Therapy System," *deepwave*, RevB/080926, 2008.

BlueCross BlueShield of Kansas City, "Percutaneous Electrical Nerve Stimulation (PENS) and Percutaneous Neuromodulation Therapy (PNT)," 7 pages, 1988.

Bodhale, D.W. et al., "Design, fabrication and analysis of silicon microneedles for transdermal drug delivery applications," *Proceedings of the 3rd International Conference on the Development of BME in Vietnam*, pp. 84-88, Jan. 11-14, 2010.

Bruce, C.J. et al., "Intracardiac Echocardiography," *European Journal Echocardiography*, vol. 2, pp. 234-244, 2001, The European Society of Cardiology.

Cabodevila, G. et al., "An overview on drug delivery using microneedles", *Institute FEMTO-ST, Dept LPMO*, 24 pages, Oct. 2005, Workshop Micro Dosing Systems.

Certified Pulsed Signal Therapy Centers, http://www.certifiedpst.com, 10 pages.

Choi, S. et al., "Microneedle Electrode Array for Electroporation of Skin for Gene Therapy," 2 pages, 2005, Controlled Release Society 32nd Annual Meeting and Exposition Transactions.

Curley, S. et al., "Radiofrequency Ablation of Unresectable Primary and Metastatic Hepatic Malignancies," *Annals of Surgery*, vol. 230(1):1-8, 1999 Lippincott Williams & Wilkins, Inc.

Ebi L.P., EBI Bone Healing System, http://www.ebimedical.com/products/fracture/bonehealing.html, 5 pages.

Fallon Community Health Plan, "Spinal Cord Stimulation," 4 pages, 2006.

Grundfest H. et al., "Stainless Steel Micro-Needle Electrodes Made by Electrolytic Pointing," *Review of Scientific Instruments*, vol. 21(4):2 pages, 1950, American Institute of Physics.

Harvinder S. Gill et al., "Effect of microneedle design on pain in human subjects," *NIH Public Access Author Manuscript*, 24(7): 585-594, Sep. 2008, Clinical Journal of Pain.

Huber, D.E. et al., "Popliteal Vein Compression Under General Anaesthesia," *European Journal of Vascular and Endovascular Surgery*, vol. 37, pp. 464-469, 2009, Elsevier Ltd.

International Patent Application No. PCT/US2007/080196 in the name of EMKINETICS, Inc. filed Oct. 2, 2007, International Search Report and Written Opinion mailed Apr. 24, 2008.

International Patent Application No. PCT/US2010/043142 in the name of EMKINETICS, Inc. filed Jul. 23, 2010, International Search Report and Written Opinion mailed Sep. 24, 2010.

International Patent Application No. PCT/US2010/043143 in the name of EMKINETICS, Inc. filed Jul. 23, 2010, International Search Report and Written Opinion mailed Sep. 15, 2010.

International Patent Application No. PCT/US2010/054167 in the name of EMKINETICS, Inc. filed Oct. 26, 2010, International Search Report and Written Opinion mailed Dec. 23, 2010.

International Patent Application No. PCT/US2010/054353 in the name of EMKINETICS, Inc. filed Oct. 27, 2010, International Search Report and Written Opinion mailed Dec. 28, 2010.

Isseroff, Roslyn R. et al., "Beta Adrenergic Receptor (βAR) Signaling as a novel target for optimizing skin wound healing", 5 pages.

Jacobson, Jerry I. et al., "Low-Amplitude, Extremely Low Frequency Magnetic Fields for the Treatment of Osteoarthritic Knees: A Double-Blind Clinical Study," *Electromagnetic Fields and Human Health. Fundamental and Applied Research*, pp. 363-364, Sep. 17-24, 2002, Proceedings of the Third International Conference.

Jasper, H. et al., "Unipolar Electromyograms of Normal and Denervated Human Muscle," pp. 231-244, Oct. 12, 1948, Department of Neurology and Neurosurgery, McGill University, and Montreal Neurological Institute.

Kravitz, S. et al., Microneedles for In-Situ/In-vivo Eecrochemical Sensor Applications, 1 page, Sandia National Laboratories.

Kurtzke, John F., "Epidemiology of Spinal Cord Injury," *IV Panamerican Congress of Neurology*, 18(2-3): 157-90, 93, 1975.

Luttge, R. "Microneedle array electrode for human EEG recording," IFMBE Proceedings 22, pp. 1246-1249, 2008, Springer-Verlag Berlin Heidelberg 2009.

McFarlane, J.P. et al., "Acute Suppression of Idiopathic Detrusor Instability with Magnetic Stimulation of the Sacral Nerve Roots," *British Journal of Urology*, 80(5): 734-41, Nov. 1997.

Morrison, P.R. et al., "Radiofrequency Ablation of Thoracic Lesions: Part I. Experiments in the Normal Porcine Thorax," *American Journal of Roentgenology*, 2005;184:375-380, Feb. 2005, American Roentgen Ray Society.

NeuroStar TMS Therapy, NeuroStar TMS Therapy® Recipient of Medical Design Excellence Award, *PRNewswire*, 3 pages, Apr. 2009.

Newmark, Inc., "Standard Products, Highest Quality Components, Designed & Produced Exclusively for Electrode Manufacturers," *Innovation by Design Newmark*, 2 pages, www.newmarkine.com/std_prods.htm, printed on May 3, 2010.

Noble, J.H. et al., "Automatic segmentation of the facial nerve and chorda tympani in CT images using spatially dependent features values", Medical Phsysics, vol. 35(12), pp. 5375-5384, Dec. 2008, American Association Physical Medicine.

Patel, G. et al., "Microneedles: The option for painless delivery," www.pharmainfo.net/reviews/microneedles-option-painless-delivery, 6 pages, printed on Sep. 9, 2008.

*PubMed, U.S. National Library of Medicine National Institutes of Health*, microneedle array electrode—Pub Med results, www.ncbi.nlm.nig.gov/sites/entrez, 2 pages, Search performed on Apr. 22, 2010.

*PubMed, U.S. National Library of Medicine National Institutes of Health*, microneedle electrode—Pub Med results, wvvw.ncbi.nlm.nig.gov/sites/entrez, 7 pages, Search performed on Apr. 22, 2010.

Schaefer, O. et al., "CT-guided radiofrequency ablation of a bronchogenic carcinoma," *The British Journal of Radiology*, 76 (2003), pp. 268-270, 2003, The British Institute of Radiology.

Shafik, Ahmed, "Magnetic Stimulation: A Novel Method for Inducing Evacuation of the Neuropathic Rectum and Urinary Bladder in a Canine Model," *Urology* 54(2): 368-372, Aug. 1999.

Sheridan, Mt. et al., "Pretreatment apoptosis in carcinoma of the cervix correlates with changes in tumour oxygenation during radiotherapy," *British Journal of Cancer*, 82(6):1177-1182, 2000 Cancer Research Campaign.

Sivagangabalan, G. et al., "Comparison of Electroanatomic Contact and Noncontact Mapping of Ventricular Scar in a Postinfarct Ovine Model With Intramural Needle Electrode Recording and Histological Validation," *Circulation: Arrhythmia and Electrophysiology, Journal of the American Heart Association*, vol. 1:363-369, 2008, American Heart Association.

Solbiati, L. et al., "Percutaneous US-guided Radio-Frequency Tissue Ablation of Liver Metastases: Treatment and Follow-up in 16 Patients," *Radiology*, 202(1):195-203, 1997 L.S. RSNA.

The Magstim Company Ltd, "Air Film Coil," *Magstim*, 4 pages, 2007.

Thon, W.F. et al., "Neuromodulation of voiding dysfunction and pelvic pain," *World Journal of Urology*, vol. 9: pp. 138-141, 1991, Springer-Verlag.

Trock, David H., "Electromagnetic Fields and Magnets Investigational Treatment for Musculoskeletal Disorders," *Rheumatic Diseases Clinics of North America*, vol. 26, No. 1., Feb. 2000.

Trock, David H., et al., "The Effect of Pulsed Electromagnetic Fields in the Treatment of Osteoarthritis of the Knee and Cervical Spine. Report of Randomized, Double Blind, Placebo Controlled Trials," *The Journal of Rheumatology*, 1903-1911, 1994.

Tyco Adhesives, "2932 Designed Adhesives," *Specialty Tape Group*, 1 page.

U.S. Appl. No. 12/815,348, filed Jun. 14, 2010 in the name of Reydel et al., non-final Office Action dated Feb. 14, 2011.

U.S. Appl. No. 10/077,434, filed Feb. 19, 2002 in the name of Burnett et al., non-fiinal Office Action mailed Jul. 2, 2003.

U.S. Appl. No. 10/077,434, filed Feb. 19, 2002 in the name of Burnett et al., Notice of Allowance mailed Oct. 17, 2003.

U.S. Appl. No. 11/332,797, filed Jan. 27, 2006 in the name of Mangrurn et al., final Office Action mailed Jul. 27, 2009.

U.S. Appl. No. 11/866,329, filed Oct. 2, 2007 in the name of Burnett et al., final Office Action mailed Mar. 16, 2010.

U.S. Appl. No. 11/866,329, filed Oct. 2, 2007 in the name of Burnett et al., non-final Office Action mailed Jun. 10, 2009.

U.S. Appl. No. 12/469,365, filed May 20, 2009 in the name of Mangrum et al., non-final Office Action mailed Aug. 27, 2010.

U.S. Appl. No. 12/695,087, filed Jan. 27, 2010 in the name of Mangrum et al., non-final Office Action mailed Dec. 23, 2010.

vanSonnenberg, E. et al., "Radiofrequency Ablation of Thoracic Lesions: Part 2, Initial Clinical Experience—Technical and Multidisciplinary Considerations in 30 Patients," *American Journal of Roentgenology*, 2005;184:381-390, Feb. 2005, American Roentgen Ray Society.

Wanich, T. et al, A Randomized Placebo-Controlled Study to Determine Safety and Efficacy in Terms of Pain Reduction, Increased Range of Motion, and Reduced Pain Medications, For A Novel Percutaneous Neuromodulation Pain Therapy Device ("Deepwave®") Following Post-Operative Treatments for Total Knee Replacement Procedures,"American Academy of Orthopaedic Surgeons 2009 Annual Meeting", 6 pages, Feb. 25-28, 2008, Biowave Corporation.

Warwick, K. et al., "The Application of Implant Technology for Cybernetic Systems," *Archives of Neurology*, vol. 60:1369-1373, Oct. 2003, American Medical Association.

Wilke, N. et al., "Fabrication and Characterisation of Microneedle Electrode Arrays using Wet Etch Technologies," 5 pages, Oct. 20-21 2004, EMN04, NMRC, University College.

Zhao, M., "Genetic Analysis of Electric Signal-directed Cell Movement," 33 pages, Apr. 8, 2008, Modelling Complex Biological Systems in the Context of Genomics.

Zoll Lifecor Corporation, "What is the LifeVest Wearable Defibrillator," http://www.lifecor.com/about_lifevest/about.asp#, 1 page, printed on Jan. 7, 2011.

U.S. Appl. No. 12/509,304, filed Jul. 24, 2009 in the name of Burnett et al., non-final Office Action mailed Feb. 14, 2011.

CystoMedix, Inc., "Percutaneous Tibial Nerve Stimulation via Urgent® PC Neuromodulation System—An Emerging Technology for managing Overactive Bladder," Business Briefing: Global Surgery, 2004.

Lin et al., "Magnetic Stimulation of the Bladder in Dogs," AAEM Annual Meeting 1993, *Muscle & Nerve*, Oct. 1993 (Abstract).

Maass et al., "Contactless Nerve Stimulation and Signal Detection by Inductive Transducer," Symposium on Application of Magnetism in Bioengineering, 1969.

Wijkstrda et al., "Selective Stimulation and Blocking of Sacral Nerves: Research Setup and Preliminary Results," Annual International Conference of the IEEE Engineering in Medicine and Biology Society, vol. 13, No. 2, 1991.

* cited by examiner

METHOD AND APPARATUS FOR MAGNETIC INDUCTION THERAPY

CROSS-REFERENCE TO RELATED APPLICATIONS

This application is a continuation of U.S. patent application Ser. No. 11/866,329 filed Oct. 2, 2007, which claims priority to U.S. Provisional Patent Application No. 60/848,720 filed Oct. 2, 2006, the contents of which are incorporated herein by reference in their entirety.

FIELD OF THE INVENTION

The present invention relates to energy emitting apparatus and methods for providing a medical therapy. In one embodiment, the energy emitting apparatus is an ergonomic wrap or cradle that contains conductive coils generating a magnetic field directed to a target nerve.

BACKGROUND OF THE INVENTION

Overactive bladder ("OAB") and urinary incontinence ("UI") affect over 16% of the American population each year, or approximately 34 million men and women. Outside of the United States, OAB and UI affects over 46 million Europeans. The economic cost of OAB and UI is estimated to be in excess of $12 billion a year in the United States alone.

Due to the social stigmas attached to OAB and UI and to misunderstandings related to the symptoms associated with OAB and UI, only 40% of the affected individuals in the United States seek medical treatment. Of those 13.6 million Americans seeking medical treatment, nearly 30% or 4 million individuals are reportedly unsatisfied with their current therapy.

Known treatments for OAB and UI include exercise and behavioral modifications, pharmacological therapies, surgical intervention and neuromodulation, but each of these treatments exhibits severe limitations.

Exercise and behavioral modifications often require patients to adhere to stringent routines, including scheduled voiding, maintenance of a bladder diary, and intense exercise regimens. While this type of treatment may be a viable option for a small group of highly dedicated individuals, its daily impact on a person's life makes it unattractive for most patients.

Pharmacological intervention is the most widely prescribed therapy for OAB and UI. Unfortunately, patients often suffer from side effects related to their drug therapies. Such side effects are sometimes serious and are particularly pronounced in elderly patient populations that tend to use a plurality of medications. In addition, approximately 30% of all patients subjected to pharmacological therapies appear to be dissatisfied with the efficacy of their prescribed treatments.

Surgical intervention IS extremely invasive and often results in a long-term requirement for catheterization that may become permanent in some instances. The negative impact of these procedures on the patient's quality of life and their high expense make surgical intervention a recommended option only when all other treatment options have been exhausted.

Neuromodulation is another available therapy for OAB and UI. In general, pulsed electromagnetic stimulation ("PES") has proven to have beneficial effects in a variety of medical applications. The related scientific principle is that an electric current passing through a coil generates an electromagnetic field, which induces a current within a conductive material placed inside the electromagnetic field.

More particularly, PES has been shown to be an effective method of stimulating a nerve positioned within the electromagnetic field, thereby affecting a muscle controlled by that nerve. For example, in the paper titled "Contactless Nerve Stimulation and Signal Detection by Inductive Transducer" presented at the 1969 Symposium on Application of Magnetism in Bioengineering, Maass et al. disclosed that a nerve threading the lumen of a toroid could be stimulated by a magnetic field of 0.7 Volt peak amplitude and a 50 μs duration in a monitor wire, and that such stimulation could generate a contraction of major leg muscles in anesthetized mammals.

Various attempts were made in the prior art to use PES for treating a variety of ailments. For example, U.S. Pat. No. 4,548,208 to Niemi discloses an apparatus for inducing bone growth by generating an electric current in the body through the external application of an electromagnetic field. Such apparatus includes opposing clamps disposed on a limb and may optionally include feedback coils and a microprocessor for sensing the magnetic field, so to avoid an overcurrent mode. Therefore, this apparatus optimizes the magnetic field on the basis of measurements of the generated magnetic field.

U.S. Pat. No. 4,940,453 to Cadwell discloses a method and apparatus for magnetically stimulating the neural pathways of a higher level organism. In this invention, a sinusoidally fluctuating current flow is created through a coil that overlies neurons to be stimulated, and frequency of the current flow and frequency of the magnetic field produced by the coil predetermined to correspond to the time constant of the neurons to be stimulated. Sensors for sensing coil conditions, such as coil temperature, may also be included.

U.S. Pat. No. 5,000,178 to Griffith discloses an electrical to electromagnetic transducer for applying electromagnetic energy to damaged parts of a living body by directing electromagnetic radiation to a certain damaged body part. Electromagnetic radiation is initially generated by a dipole consisting of a bar of high permeability material wrapped with an electrically conductive coil. Magnetic fields, which are generated away from the damaged body part, intersect a conductive shield and establish eddy currents, which in turn generate magnetic fields opposite and nearly equal to the magnetic fields generated by the electromagnetic source. The resultant electromagnetic fields reinforce the electromagnetic field directed towards the damaged body part and diminish the electromagnetic field directed away from the damaged body part.

U.S. Pat. No. 5,014,699 to Pollack et al. discloses a non-invasive, portable electromagnetic therapeutic method and apparatus for promoting the healing of damaged or diseased living tissue, including fractured bone. These method and apparatus involve generating a signal that has a series of substantially symmetric voltage cycles of bursted pulses with narrow pulse widths of 0.5 to 20 microseconds, and further involve converting the signal into an electromagnetic field extending into an area that contains tissue to be healed. This invention provides for no feedback on the efficiency of the applied stimulation.

In a paper titled "Selective Stimulation and Blocking of Sacral Nerves: Research Setup and Preliminary Results," published in Annual International Conference of the IEEE Engineering in Medicine and Biology Society, Vol. 13, No. 2, 1991, Wijkstrda et al. used an external pulsed magnetic coil to stimulate a peripheral nerve for the treatment of urinary incontinence. The authors used a large magnetic field produced by a single coil to ensure that the nerve was fired and the resulting nerve conduction was frequently painful or intolerable. In addition, coil alignment was problematic because an internally implanted coil was utilized, which had to be aligned with the fully external magnetic field to stimulate the nerve. Due to the difficulty in positioning the device, the practical application of this therapy does not permit home healthcare usage without a preset alignment and monitoring of the nerve, and no provision was made to insure that the nerve was actually being stimulated or to adjust the device in response to commonly occurring physiologic and anatomic variations in nerve locations.

U.S. Pat. Nos. 5,181,902 Erickson et al. and 5,314,401 to Tepper disclose pulsed electromagnetic field ("PEMF") transducer systems usable to perform PEMF therapies (such as after spinal fusion) by generating flux-aided electromagnetic fields. The drive electronics includes a PEMF processor that executes a PEMF program for controlling the activation of the electromagnetic fields (field strength and cycle).

In a paper titled: "Magnetic Stimulation of the Bladder in Dogs" presented at the 1993 AAEM Annual Meeting, the abstract of which was published in the Muscle & Nerve issue of October 1993, Lin et al. disclosed that magnetic stimulation could be employed to stimulate the cortex, spinal nerves and peripheral nerves of dogs through direct trans-abdominal stimulation of the detrusor muscles or through stimulation of the lumbosacral roots.

As shown, the prior art makes no provision to measure the efficacy of PES treatment, causing patients to be treated improperly, either by an insufficient or excessive exposure to PES. Other attempts to monitor PES dosage in the prior art exhibit serious drawbacks. For example, U.S. Pat. No. 5,518,495 to Kot discloses an apparatus for the treatment of arthritis utilizing a magnetic field therapy, which includes an adjustable voltage source that is connected to a source of line voltage and a coil connected to the adjustable voltage source. This apparatus has no feedback system to advise a healthcare provider of the efficiency of the treatment.

U.S. Pat. No. 5,984,854 to Ishikawa et al. discloses a method for treating urinary incontinence based on delivering a train of current pulses through one or more magnetic stimulation coils so to induce a train of magnetic flux pulses, which then induce an eddy current within the body and stimulates a group of pelvic floor muscles, the pudendal nerve, the external urethral sphincter, or the tibial nerve. While this method includes the use of pulsed electromagnetic for treating urinary incontinence, no specific components are envisioned to facilitate the placement of the magnetic coils over a targeted region of the body or a system for monitoring the efficiency of the therapy being applied.

U.S. Pat. No. 6,086,525 to Davey et al. discloses a magnetic nerve stimulator that includes a core constructed from a material having a high field saturation having a coil winding disposed thereon. A thyristor capacitive discharge circuit pulses the device, and a rapidly changing magnetic field is guided by the core, preferably made from vanadium pennendur.

U.S. Pat. No. 6,701,185 to Burnett et al. also discloses an electromagnetic stimulation device that includes a plurality of overlapping coils, which can be independently energized in a predetermined sequence such that each coil will generate its own independent electromagnetic field and significantly increase the adjacent field. Unfortunately, none of these patents provides a system for monitoring the efficiency of the therapy in progress, either with respect to the proper positioning of the winding over the area to be treated or of the intensity of the magnetic field to be applied.

Other PES therapies require the implantation of devices into the patient, with the consequent discomfort, risk and cost to the patient. For example, U.S. Pat. No. 6,735,474 to Loeb et al. discloses a method and system for treating UI and/or pelvic pain by injecting or laparoscopically implanting one or more battery-or radio frequency-powered microstimulators that include electrodes placed beneath the skin of the perineum and/or adjacent the tibial nerve.

U.S. Pat. 6,941,171 to Mann et al. describes a method and a system for treating incontinence, urgency. frequency, and/or pelvic pain that includes implantation of electrodes on a lead or a discharge portion of a catheter adjacent the perineal nerve(s) or tissue(s) to be stimulated. Stimulation pulses, either electrical or drug infusion pulses, are supplied by a stimulator implanted remotely through the lead or catheter, which is tunneled subcutaneously between the stimulator and stimulation site.

Other PES therapies in the prior art involve the use of electrodes placed on or beneath the skin of a patient. Recent data on invasive, needle-based PES of the posterior tibial nerve in individuals with OAB and UI indicates that PES can modulate bladder dysfunction through its action on the pudendal nerve and the sacral plexus, which provide the major excitatory input to the bladder.

In a paper titled "Percutaneous Tibial Nerve Stimulation via Urgent® PC Neuromodulation System—An Emerging Technology for managing Overactive Bladder," which was published in Business Briefing: Global Surgery 2004, CystoMedix, Inc. disclosed that peripheral tibial nerve stimulation ("PTNS") had been found effective in treating OAB. The disclosed procedure involved the use of electrode and generator components, including a small 34-gauge needle electrode, lead wires and a hand-held electrical generator. However, the procedure requires the permanent implantation of an electrical stimulation device in the patient. One estimate put the cost of treatment at nearly $14,000 with additional routine care costs of $593 per patient per year. Additionally, risks of battery failure, implant infection, and electrode migration led to a high re-operation rate and made this procedure unattractive.

U.S. Pat. No. 7,117,034 to Kronberg discloses a method for generating an electrical signal for use in biomedical applications that includes two timing-interval generators. In this invention, skin-contact electrodes may be placed over an area of interest and a microprocessor may direct timing and sequencing functions, although such timing and sequencing functions are not related to the actual efficacy of the treatment while treatment is being performed.

U.S. Patent Application Publication No. 2005/0171576 to Williams et al. discloses an electro-nerve stimulation apparatus that includes a pulse generator, a first electrically conductive, insulated lead wire, a second electrically conductive, insulated lead wire, an electrically conductive transcutaneous electrode and an electrically conductive percutaneous needle electrode. Connected to one end of the first and second lead wires is a connector for electrically coupling with the pulse generator. In this invention, a percutaneous needle electrode is inserted through the skin in proximity to the desired internal stimulation site and electric stimulation is employed, rather than pulsed electromagnetic stimulation. Moreover, the Williams invention does not contemplate mechanisms for facilitating use of the device by an untrained user, nor a monitoring of the applied therapy.

A neuromodulation alternative is a posterior tibial nerve stimulator, often referred to as SANS, but as is the case with other forms of neuromodulation, this procedure is invasive in nature and requires the insertion of a needle five centimeters into the patient's ankle region to stimulate the posterior tibial nerve. This procedure also requires a minimum of twelve sessions for initial treatment, possibly with additional sessions required for maintenance.

SUMMARY OF THE INVENTION

It is an object of the present invention to provide apparatus and methods for magnetic induction therapy, in which dosage of magnetic energy can be regulated according conduction in a target nerve exposed to the magnetic field.

It is another object of the present invention to provide apparatus and methods for magnetic induction therapy, in which the flow of magnetic energy can be adjusted directionally by the patient or a healthcare provider without altering the position of a housing containing conductive coils that produce the magnetic field.

It is a further object of the present invention to provide apparatus and methods for treating a variety of ailments by providing energy to a target nerve, for example magnetic energy, electrical energy or ultrasound energy, at a location and in an amount optimized by detecting conduction in the target nerve.

These and other objects of the present invention are achieved by providing an energy emitting apparatus for delivering a medical therapy that includes one or more energy generators, a logic controller electrically connected to the one or more energy generators, and one or more sensors for detecting electric conduction in a target nerve, which are connected to the logic controller. The one or more energy generators produce energy focused on the target nerve upon receiving a signal from the logic controller, and the applied energy is varied by the logic controller according to an input provided by the one or more sensors based on electric conduction in the target nerve. The feedback provided by the sensors to the logic controller about the efficacy of the applied treatment causes the logic controller to modulate the current transmitted to the coils.

The applied energy may be a magnetic field, an electrical field, an ultrasound, a visible light, or an infrared or an ultraviolet energy. When a magnetic field is applied, the energy-emitting device is an apparatus that provides a magnetic induction therapy and that includes one or more conductive coils disposed in an ergonomic housing. A logic controller is electrically connected to the one or more coils, and one or more sensors detect electric conduction in the target nerve and are connected to the logic controller so as to provide a feedback to the logic controller. The conductive coils receive an electric current from the logic controller and produce a magnetic field focused on a target nerve, and the electric current fed by the logic controller is varied by the logic controller according to an input provided by the sensors, thereby causing amplitude, frequency or direction of the magnetic field, or the firing sequence of the one or more coils, to be varied according to the efficiency of the treatment provided to the target nerve. In different embodiments of the invention, the housing containing the conductive coils may be a flexible wrap, a cradle or a garment, and the coils may be overlapping and/or be disposed in different positions within the housing, so to generate a magnetic field on different body parts with the desired direction and amplitude.

The one or more coils may be stationary or movable within the housing, making it possible to optimize the direction of magnetic flow to the target nerve by disposing the coils in the most effective direction. In different embodiments, the coils may be movable manually by acting on a knob, lever, or similar type of actuator, or may be translated automatically by the logic controller in response to the input provided by the sensors. When a preferred position for the coils has been established, the coils may be locked in position and maintain that position during successive therapy sessions. In other embodiments, the sensors may be incorporated within the housing, or instead may be disposed on a body part of interest independently of the housing.

In still other embodiments of the invention, the inductive coils are disposed in a housing that is situated externally to a patient's body, and additional inductive coils are implanted into the body of the patient and are magnetically coupled to the external inductive coils. With this coil arrangement, energy may be transmitted from the external coils to the internal coils either to recharge or to activate an implantable device. In yet other embodiments of the invention, the electric current may varied by the logic controller both on the basis of an input provided by the one or more sensors and also an input provided by the patient according to a muscular response she has perceived, for example, the twitching of a toe after application of the magnetic field.

In yet other embodiments of the invention, the source of energy for nerve stimulation may be electrical energy and nerve conduction may be detected at a site sufficiently distant from the site of stimulation, so to enable detection of nerve conduction despite the confounding interference from the direct electrical stimuli. In these embodiments, direct electrical stimulation of nerve and muscle may be tailored to provide optimal therapy and, in the case of electrode migration or other electrode malfunction, to report lack of stimulation of the bodily tissues. Furthermore, these embodiments enable a reduction in power requirement, because control of the signal is provided by the sensor to the signal generator loop.

Methods of use of the above apparatus are also described herein.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1:
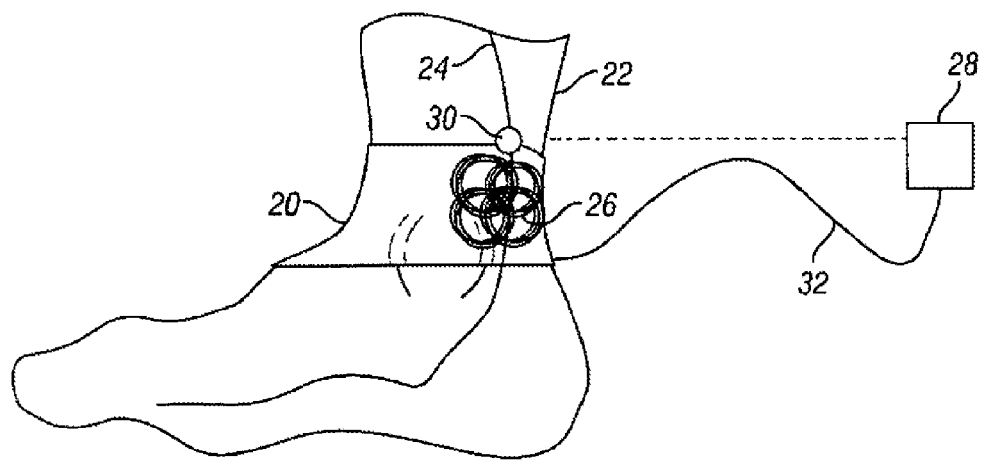
FIG. 1 is a schematic view of an apparatus for magnetic induction therapy according to a first embodiment of the invention.

Referring first to FIG. 1, a first embodiment of the invention includes a coil wrap 20, which is depicted as disposed over ankle 22 circumferentially to surround a portion of tibial nerve 24. Because tibial nerve 24 is targeted, this embodiment is particularly suited for the treatment of OAB and VI. In other embodiments of the invention, coil wrap 20 may be configured to surround other body parts that contain a portion of tibial nerve 24 or of other nerves branching from or connected to tibial nerve 24, still making these embodiments suitable for treating OAB and VI. In still other embodiments of the invention, coil wrap 20 may be configured for surrounding body parts that contain other nerves when treatments of other ailments are intended.

Coil wrap 20 may be manufactured from a variety of materials suitable for wearing over ankle 22. Preferably, coil wrap is produced from a soft, body-compatible material, natural or synthetic, for example, cotton, wool, polyester, rayon, Gore-Tex®, or other fibers or materials known to a person skilled in the art as non-irritating and preferably breathable when tailored into a garment. Coil wrap 22 may even be manufactured from a molded or cast synthetic material, such as a urethane gel, to add extra comfort to the patient by providing a soft and drapable feel. Additionally, coil wrap 20 may be produced from a single layer of material or from multiple material layers and may include padding or other filling between the layers.

Coil wrap 20 contains one or more conductive coils 26 arranged to produce a pulsed magnetic field that will flow across tibial nerve 24 and generate a current that will flow along tibial nerve 24 and spread along the length of tibial nerve 24 all the way to its sacral or pudendal nerve root origins. Coils 26 may be a single coil shaped in a simple helical pattern or as a figure eight coil, a four leaf clover coil, a Helmholtz coil, a modified Helmholtz coil, or may be shaped as a combination of the aforementioned coils patterns. Additionally, other coil designs beyond those mentioned hereinabove might be utilized as long as a magnetic field is developed that will encompass tibial nerve 24 or any other target nerve. When a plurality of coils is utilized, such coils may be disposed on a single side of ankle 22, or may be disposed on more than one side, for example, on opposing sides, strengthening and directionalizing the flow of the magnetic field through tibial nerve 24 or other peripheral nerves of interest.

Coil wrap 20 is preferably configured as an ergonomic wrap, for example, as an essentially cylindrical band that can be pulled over ankle 22, or as an open band that can be wrapped around ankle 22 and have its ends connected with a buckle, a hoop and loop system, or any other closing system known to a person skilled in the art. By properly adjusting the position of coil wrap 20 over ankle 22, a patient or a health care provider may optimize the flow of the magnetic field through tibial nerve 24, based on system feedback or on sensory perceptions of the patient, as described in greater detail below.

The electric current that produces the magnetic field by flowing through coils 26 is supplied by a programmable logic controller 28, which is connected to coils 26, for example, with a power cord 32. A sensor 30 that feeds information to logic controller 28 is also provided, in order to tailor the strength of the magnetic field and control activation of coils 26 based on nerve conduction. The purpose of sensor 30 is to detect and record the firing of the target nerve and to provide related information to logic controller 28, so to render the intended therapy most effective. For example, sensor input may cause logic controller 28 to alter the strength or pulse amplitude of the magnetic field based on sensor input, or fire the coils in a certain sequence.

In this embodiment, as well as in the other embodiments described hereinafter, sensor 30 may include one or more sensor patches and may be placed at different distances from the region of direct exposure to the magnetic field. For example, sensor 30 may be configured as a voltage or current detector in the form of an EKG patch and may be placed anywhere in the vicinity of the target nerve to detect its activation. For ease of description, the term "coils" will be used hereinafter to indicate "one or more coils" and "sensor" to indicate "one or more sensors," unless specified otherwise.

By virtue of the above described arrangement, coil wrap 20 provides a reproducibly correct level of stimulation during an initial therapy session and during successive therapy sessions, because the presence or absence of nerve conduction is detected and, in some embodiments, measured when coil wrap 20 is first fitted and fine-tuned on the patient. In addition to properly modulating the applied magnetic field, the positioning of coils 26 over ankle 22 may also be tailored according to the input provided by sensor 30, so to fine-tune the direction of the magnetic field. Such an adjustment of the direction, amplitude, and level of the stimulation provided to the target nerve through the above described automated feedback loop, to ensure that peripheral nerve conduction is being achieved, is one of the key features in the present invention.

If the magnetic pulse does not substantially interfere with sensor 30, sensor 30 may be placed directly within the field of stimulation, so that power supplied to the system may be conserved. This is particularly important for battery-powered systems. Alternatively, sensor 30 may also be placed at a distance from the magnetic field and still properly detect neural stimulation.

In a method of use of coil wrap 20, the amplitude and/or firing sequence of coils 26 may be ramped up progressively, so that the magnetic field is increased in strength and/or breadth until nerve conduction is detected, after which the applied stimulus is adjusted or maintained at its current level for the remainder of the therapy. The level of stimulation may be also controlled through a combination of feedback from sensor 30 and feedback based on perceptions of the patient. For example, the patient may activate a switch once she perceives an excessive stimulation, in particular, an excessive level of muscular stimulation. In one instance, the patient may be asked to push a button or turn a knob when she feels her toe twitching or when she experiences paresthesia over the sole of her foot. The patient will then continue pressing the button or keep the knob in the rotated position until she can no longer feel her toe twitching or paresthesia in her foot, indicating that that level of applied stimulation corresponds to an optimal therapy level. From that point on, the patient may be instructed to simply retain her foot, knee, or other limb within coil wrap 20 until therapy has been terminated while the system is kept at the optimal level. Adding patient input enables control of coil wrap 20 during outpatient treatments, because the patient is now able to adjust the intensity of the magnetic field herself beyond the signals provided to logic controller 28 by sensor 30.

Detecting and, if the case, measuring conduction in one or more nerves along the conduction pathways of the stimulated nerve confirms that the target nerve has been stimulated, providing an accurate assessment of the efficiency of the applied therapy on the patient. A concomitant detection of muscle contraction may also confirm that the target nerve is being stimulated and provide an indication to the patient or to a healthcare provider as to whether stimulation has been applied at an excessive level in view of the anatomical and physiological characteristics of the patient.

Based on the foregoing, coil wrap 20 allows for a consistent, user-friendly targeting and modulation of the peripheral nerves via the posterior tibial nerve on an outpatient basis, in particular, the targeting and modulation of the pudendal nerve and of the sacral plexus. When multiple coils 26 are present, coils 26 may be activated simultaneously or differentially to generate the desired magnetic field. The direction and location of each of coils 26 may be reversibly or irreversibly adjusted by the healthcare provider or by the patient, customizing the location of the applied stimulation to the anatomy and therapy needs of each patient. After a healthcare provider has optimized position and firing sequence for each of coils 26, the patient may be sent home with coil wrap 20 adjusted to consistently target the desired nerve. In one variant of the present embodiment, an automatic feedback system adjusts one or more of firing sequence, firing strength or position of coils 26 within coil wrap 20 during the initial setup and also during successive therapy sessions.

In summary, the teachings of the present invention include the creation of a loop consisting of feeding information on nerve conduction to logic controller 28 and on logic controller 28 tailoring the electrical current sent to coil wrap 20 according to the information received from sensor 26 based on whether or not the nerve is receiving the desired stimulation and, in some embodiments, the desired amount of stimulation. This arrangement offers an unparalleled level of therapy control and flexibility within a home care setting, because a consistent, repeatable stimulation of the target nerve can be attained. Aside from adjusting the position of coils 26 in accordance with the patient's anatomy and physiological variations, controlling pulse amplitude is also of great importance even during different therapy sessions with the same patient. For example, a patient with leg edema will encounter difficulties in properly adjusting coil wrap 20 based on whether her legs and ankles are swollen or not swollen, and the power required to penetrate to posterior tibial nerve 24 (in the case of a VI therapy) will vary greatly due to the variable depth of the nerve. Thus, having feedback provided by sensor 26 becomes a necessity for achieving an accurate dosage of the treatment rather than an option. Benchtop testing has demonstrated that a system constructed according to the present invention is capable of non-invasively generating electrical currents similar to those found in therapeutic electro-stimulation and to do so in different settings.

Figure 2:
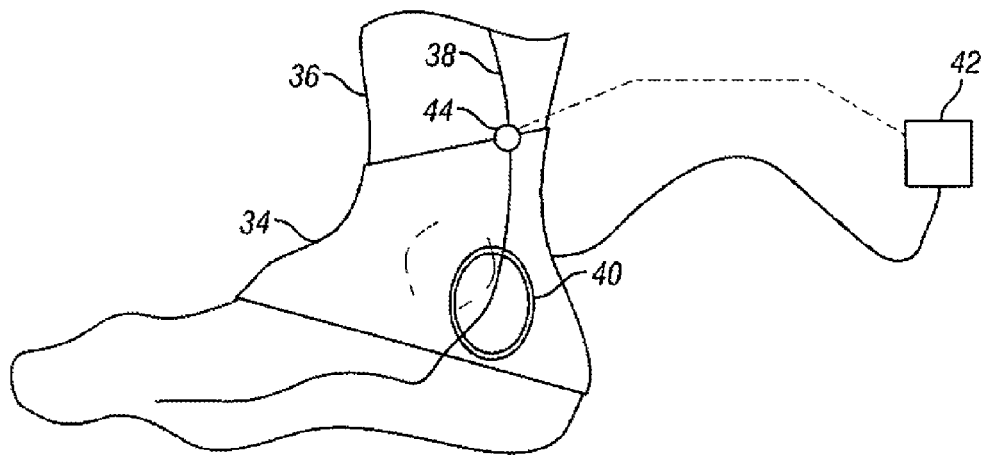
FIG. 2 is a schematic view of an apparatus for magnetic induction therapy according to a second embodiment of the invention.

Referring now to FIG. 2, a second embodiment of the invention will be described with reference to a coil wrap 34 disposed over ankle 36 for the purpose of treating VI by targeting tibial nerve 38. In this second embodiment, one or more Helmholtz coils 40 are disposed within coil wrap 34 to create a more narrowly directed magnetic field over tibial nerve 38. Like in the all other embodiments described herein, more than one coil (in the present embodiment, more than one Helmholtz coil 40) may be placed within coil wrap 34 and be disposed in different positions within coil wrap 34, in order to optimize magnetic flux over tibial nerve. For example, two Helmholtz coils may be disposed one opposite to the other within coil wrap 34.

Having coil windings arranged along a common longitudinal axis, as required in a Helmholtz coil configuration, generates a more focused magnetic field and a more accurate targeting of tibial nerve 38 or of any other nerve. Like in the previous embodiment, the operation of coils 40 is controlled by a logic controller 42, which is in turn connected to sensor 44 that monitors conduction in tibial nerve 44 and that generates a feedback to logic controller 42 about the efficiency of the therapy in progress. Therefore, like in the previous embodiment, the coupling of sensor 44 with logic controller 42 optimizes operation of coil wrap 34 according to results measured at the level of tibial nerve 38. Also like in the previous embodiment, manual adjustments to the parameters of electric current provided by logic controller 42 to Helmholtz coil 40 may also be made manually by the patient or by a healthcare provider, and coil wrap 34 may be structured so that the position of Helmholtz coil 40 within coil wrap 34 is adjusted as desired either manually by the patient or by a healthcare provider, or automatically by logic controller 42.

Figure 3:
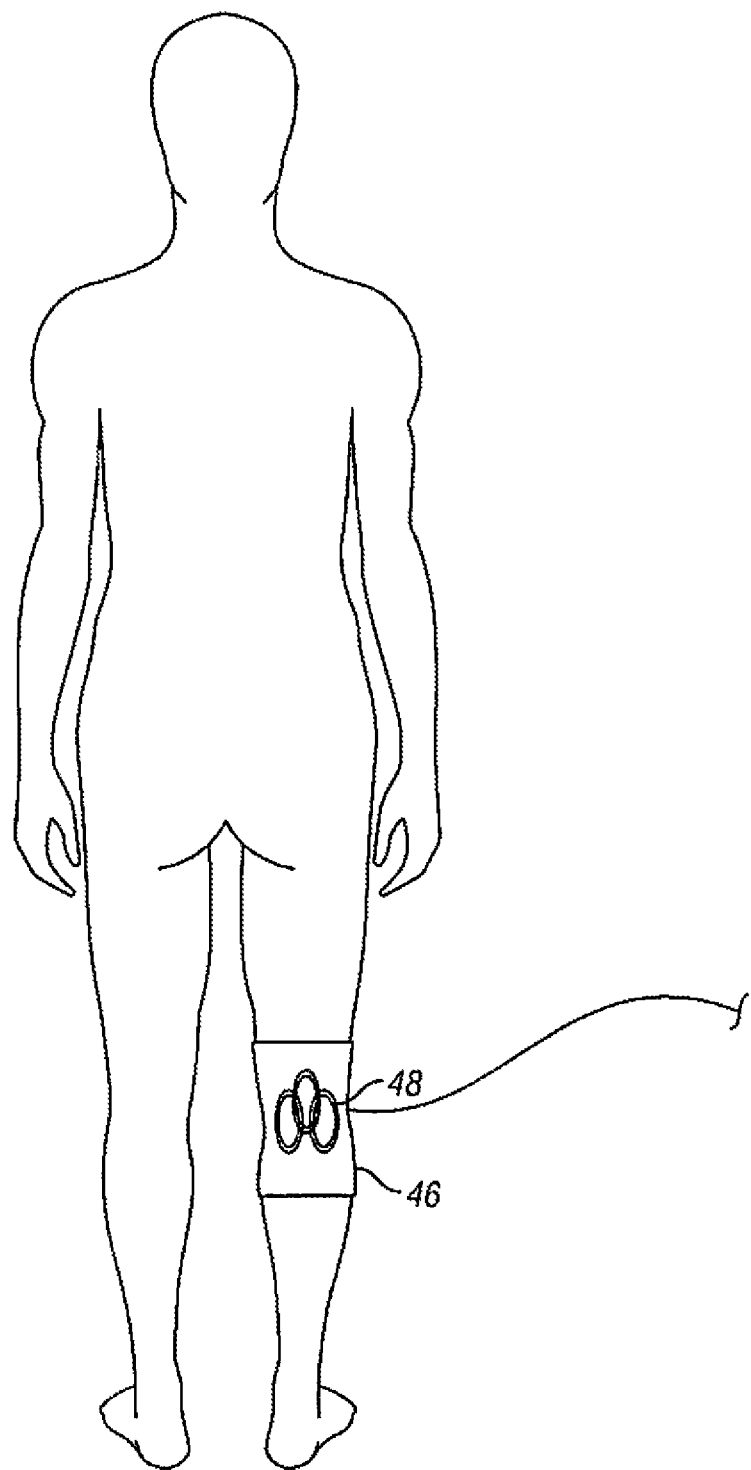
FIG. 3 is a schematic view of an apparatus for magnetic induction therapy according to a third embodiment of the invention.

Referring now to FIG. 3, a third embodiment of the invention includes a coil wrap 46 configured for wrapping over the popliteal fossa of a patient, in the region of the knee, to stimulate the posterior tibial nerve (not shown). The configuration and structure of coil wrap 46 reflect the body portion covered by coil wrap 46, but the key system components of coil wrap 46, such as the type, number and disposition of the coils (for example, the use of overlapping coils); the connections of the coils with a logic controller; and the use of one or more sensors (also not shown) to detect nerve conduction are all comparable to those in the previously described embodiments.

Figure 4:
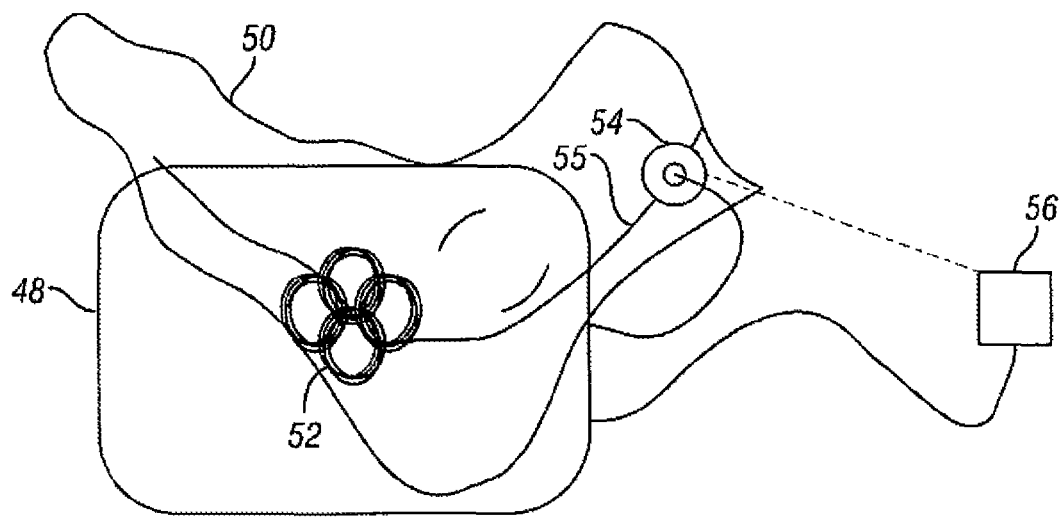
FIG. 4 is a schematic view of an apparatus for magnetic induction therapy according to a fourth embodiment of the invention.

Referring now to FIG. 4, a fourth embodiment of the invention includes a footrest or foot cradle 48, which is structured to contain at least a portion of a foot 50. One or more coils 52 are enclosed within cradle 48, and a sensor 54 is disposed along the pathway of tibial nerve 55, sensing conduction in tibial nerve 55, and is also connected to a logic controller 56. Coils 52, sensor 54 and logic controller 56 may be arranged in different configurations, in the same manner as in the preceding embodiments.

Cradle 48 may be made from a variety of materials and may be monolithic, or have a hollow or semi-hollow structure to enable the movement of coils 52 within cradle 48, as described in greater detail below. Preferably, cradle 48 has an ergonomically design allowing the ankle and heel of the patient to be retained within cradle 48, in a position that matches the positions of stimulating coils 52 to the area of stimulation. The design of cradle 48 provides for a particularly comfortable delivery of therapy to patients that prefer to remain seated during their therapy, and enables the patient to perform the required therapy within a health care facility, or to take cradle 48 home, typically after an initial session and appropriate training in a health care facility. In that event, the patient will be trained to apply sensor 54 autonomously and to adjust stimulation to a comfortable level.

FIG. 4 shows coils 52 disposed as overlapping and the use of a single sensor patch 54 positioned proximally to the stimulation site. However, coil 52 may be configured as a single coil, a figure eight coil, a four leaf clover coil, a Helmholtz coil, a modified Helmholtz coil or a any combination of the aforementioned coils, or as any other coil design providing an effective stimulation to the target nerve. In addition, coils 52 may be fired individually, sequentially or simultaneously according to the feedback provided by sensor 54.

In one variant of this embodiment, sensor 54 may include a conductive electrode patch that provides a feedback to logic controller 56 for adjusting, if necessary, the stimulation parameters of coils 52. Alternatively, sensor 54 may be a sensor patch that is either applied to the skin of the patient or is incorporated within the structure of cradle 48.

Figure 5:
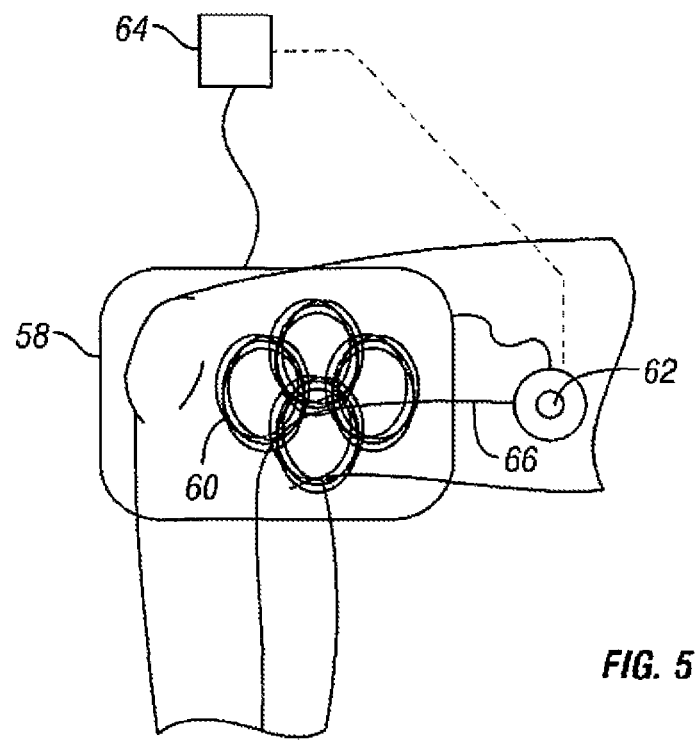
FIG. 5 is a schematic view of an apparatus for magnetic induction therapy according to a fifth embodiment of the invention.

Referring now to FIG. 5, a fifth embodiment of the invention includes a knee rest or knee cradle 58 that contains one or more conductive coils 60, one or more sensors 62 and a logic controller 64. The components of this embodiment are similar to those described with reference to the preceding embodiments, as regards the structure and materials of cradle 58, the nature and disposition of coils 60, the type and operation of sensor 62, and the function and operation of logic controller 64. Cradle 58 is configured to target the popliteal fossa of the patient, thus to target tibial nerve 66. In that respect, the present embodiment is similar to the embodiment illustrated in FIG. 3, but while the embodiment of FIG. 3 is configured as a wrap that may be worn while the patient is standing, the present embodiment is configured as a cradle that is more suited for treatment while the patient is sitting or laying down.

A method of use of the foot cradle depicted in FIG. 4 is described with reference to FIGS. 6A-6D. During a first step illustrated in FIG. 6A, foot 68 is disposed in cradle 70 that contains one or more conductive coils 72, which are connected to a logic controller (not shown) that manages the flow of electric power to coils 72.

Figure 6A:
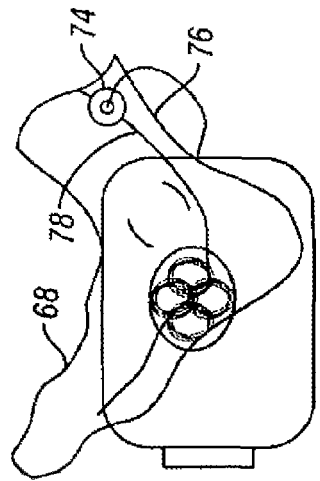
FIGS. 6A-6D are schematic illustrations depicting a first method of use of an apparatus for magnetic induction therapy. This method is based on adjusting the position of the conductive coils so to optimize a magnetic flow applied to a target nerve.
Figure 6B:
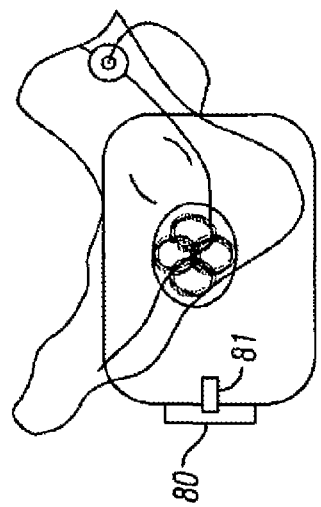

During a second step illustrated in FIG. 6B, a sensor 74 is disposed on foot 68 or on ankle 76 or on another appropriate portion of the patient's body, in order to detect conductivity in tibial nerve 78 or in another target nerve.

Figure 6C:
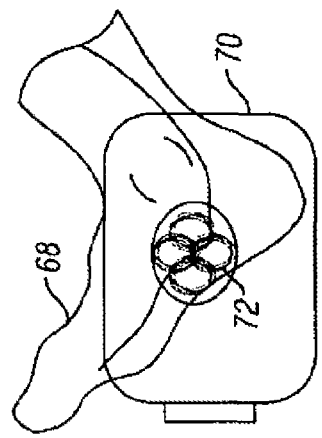

During a third step illustrated in FIG. 6C, a healthcare provider analyzes conductivity measurements provided by sensor 74 (for example, by reading gauge 77) and first adjusts the positioning of coils 72 until conduction in nerve 78 is detected. For example, the healthcare provider may rotate a knob 80, slide a lever or actuate any other displacement system for coils 72 that is known in the art, so that coils 72 are translated until a magnetic field of the proper amplitude and intensity is applied to cause conduction in nerve 78. The position of coils 72 is then fine-tuned manually until an optimal level of conduction in nerve 78 is attained, and the therapy is continued for a length of time as prescribed by the attending healthcare provider.

Figure 6D:
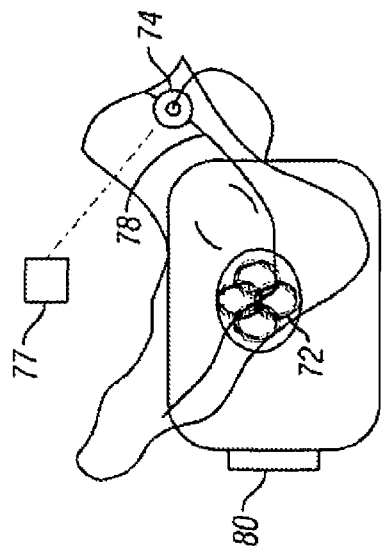

During a fourth, optional step illustrated in FIG. 6D, settings for successive therapy sessions are set, for example by locking knob 80 (in one embodiment, with a pin 81) so that the healthcare provider or the patient repeat the therapy using the predetermined settings. Alternatively, the patient may be trained to adjust the amplitude and/or strength of the applied magnetic field, as each therapy session requires.

While the present method has been described with regard to foot cradle 70, the same method steps may be envisioned for coil wraps or cradles of different configurations, for example, for the coil wraps and cradles described with reference to the previous figures.

In an alternative embodiment, the logic controller (not shown) may automatically adjust coil positioning to optimize therapy during the initial and successive sessions. While this set-up may be more difficult to implement, it also provides for an accurate targeting of the target nerve during each therapy session, regardless of alterations in patient positioning or changes to the anatomy of the patient (for example, when a foot is swollen). In this embodiment, the device simply varies the orientation of coils 84 until stimulation has been sensed.

Further, coils 84 may be translated along a single direction (for example, horizontally) or along a plurality of directions, to provide for the most accurate positioning of coils 84 with respect to the target nerve.

A second method of use of the foot cradle depicted in FIG. 4 is described now with reference to FIG. 7. While this second method is also described with reference to a foot cradle 82 employing one or more coils 84 that have a reversibly lockable, adjustable orientation, the present method may be equally implemented with a body-worn coil wrap, such as those described with reference to the previous figures, or to other embodiments of the invention. In this method, the patient or the healthcare provider adjusts the positioning of coils 84 to detect conductivity in target nerve 89.

The position of coils 84 may be translated in different directions (in the illustrated embodiment, may be translated horizontally) and may be locked in an initial position once conduction in nerve 89 is detected by a sensor (for example, sensing patch 86)

Figure 7A:
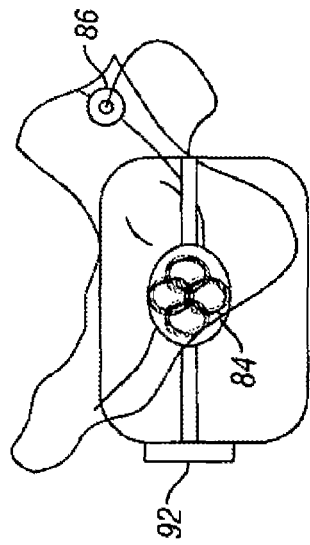
FIGS. 7A-7D are schematic illustrations of a second method of use of an apparatus for magnetic induction therapy. This method is based on locking the conductive coils in position once electrical conduction in a target nerve has been detected.
Figure 7B:
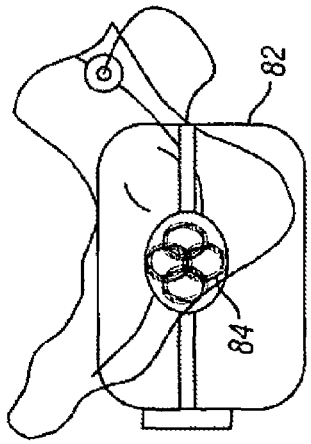

More particularly, FIG. 7A illustrates the initial positioning of foot 88 into cradle 82 and of sensor patch 86 on ankle 90 or other appropriate body part of the patient. After proper positioning of foot 88 is attained, a knob 92 (or other equivalent device) may be employed to adjust the position of coils 84, based on the signals (for example, nerve conduction signals) provided by sensor patch 86, as shown in FIG. 7B.

Figure 7C:
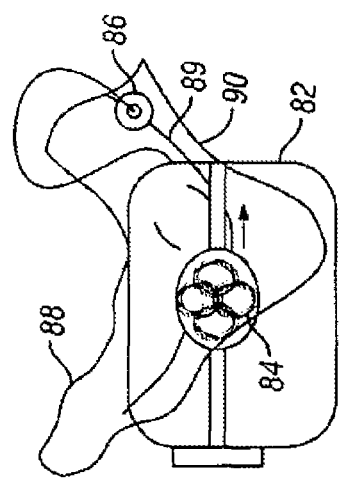
Figure 7D:
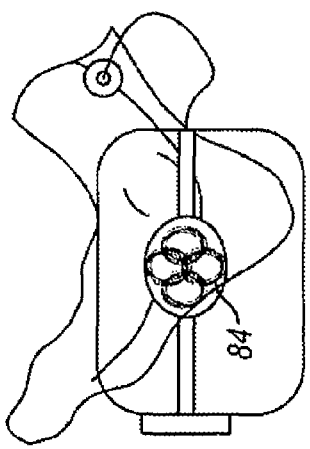

With reference to FIG. 7C, after neural conduction is detected, coils 84 are locked in place, and, with further reference to FIG. 7D, foot cradle 82 retains coils 84 locked in position for further use in a home or healthcare office environment. Therefore, in the present method, the patient or a healthcare provider simply adjusts coil position by sliding coils 84 back and along one axis until electric conduction in the target nerve is detected, although adjustments along all three axes may be possible in different variants of the present embodiment.

Figure 8:
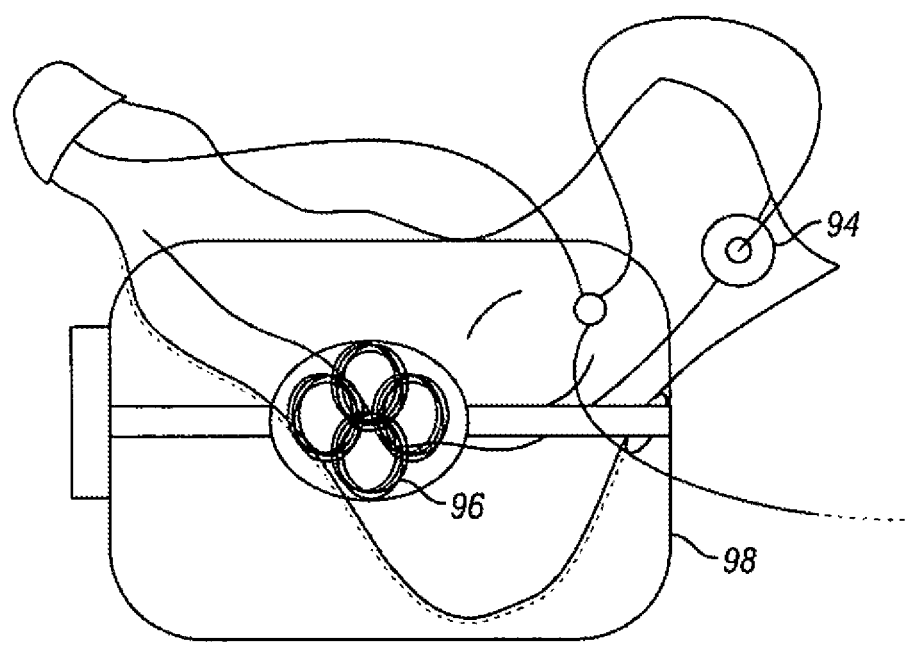
FIG. 8 is a schematic view of an embodiment of the invention that includes a plurality of sensors.

Referring now to FIG. 8, a sixth embodiment of the invention relates to the use of multiple sensors. While FIG. 8 depicts an embodiment shaped as a foot cradle 98, it should be understood that the following description also relates to any other design, whether shaped as a cradle or a wrap or otherwise. The plurality of sensors 94 described herein may detect a variety of physiologic changes, including neural impulses, muscular contraction, twitching, etc. that may occur with neural or muscular stimulation.

One or more of the illustrated sensors 94 may be employed over body regions being stimulated (for example, back, leg, arm, neck, head, torso, etc.) and may be either incorporated within an actual cradle or wrap or, otherwise, be applied separately from the cradle or the wrap.

Sensors 94 may be structured as disposable, single-use, EKG-type patches that are attached to the body outside of cradle 98 along the nerve conduction pathway and are then connected to the logic controller (not shown) before beginning therapy. This arrangement provides for an intimate body contact of sensors 94 without the risk of infection or other detrimental side effects that may be present with transcutaneous devices. Sensors 94 may be employed both for beginning and for monitoring the stimulation therapy, more specifically, sensors 94 may be employed during the beginning of the therapy to optimize the strength of the magnetic field and/or to adjust the positioning of coils 96 within the cradle 98. Once therapy has begun, sensors 94 continue to monitor nerve conduction to ensure that the correct level of stimulation is being provided. In the event that for some reason nerve conduction decays during therapy, the logic controller can automatically adjust the magnetic field, ensuring that the appropriate therapy is delivered for the appropriate amount of time.

One or more of sensors 94 in this embodiment, or any of the embodiments described herein, may take the form of an inductive coil designed to receive impulses from the underlying nerves, so that inductive technologies may be used to both stimulate the nerve or tissues as well as to record the effect of the stimulation on nerves or tissues. Any of sensors 94 may be connected to the logic controller through one or more connection modes, including, but not limited to, wireless signals, wired signals, radio frequencies, Bluetooth, infrared, ultrasound, direct switching of the current circuit, etc., so long as communication between the sensor and the device is effective.

During implementation of the present method, a healthcare provider may simply elect to use sensors 94 to adjust the device, for example, to lock coils 96 into position, during the first therapy session and not require the use of sensors 94 during each successive therapy session.

Referring now to FIGS. 9A-9D, there are shown different, non-limiting embodiments of the invention shaped as body worn ergonomic applicator garments. Each of these embodiments is shown with overlapping coils, although coils of any configurations may be used. Each of the wraps of FIGS. 9A-9D corresponds to a coil wrap, into which a body part may be placed. These garments contain one or more sensors (not shown) that provide feedback to a logic controller (also not shown), or sensors may be applied separately from those garments. Systems may also be included for reversibly or irreversibly locking the coils within the applicator.

Figure 9A:
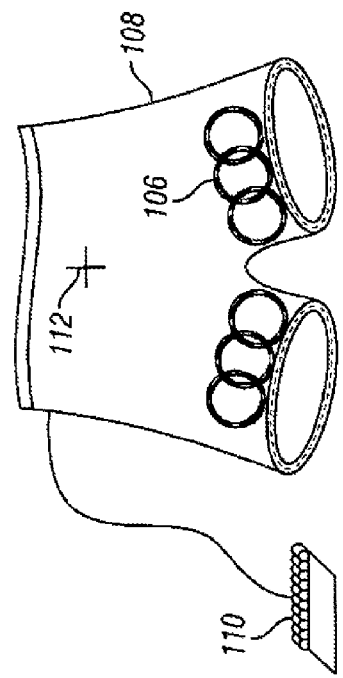
FIGS. 9A-9D are schematic representations of different garments adapted to operate as apparatus for magnetic induction therapy according to the principles of the present invention.
Figure 9B:
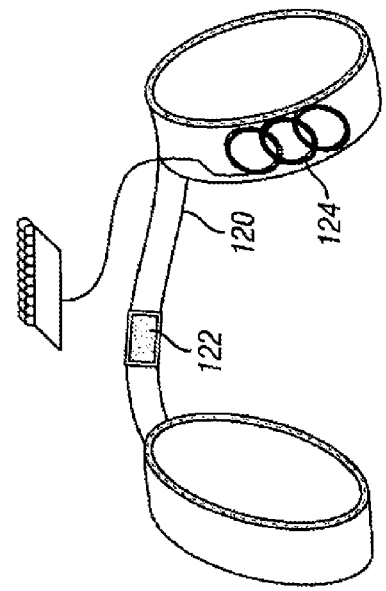
Figure 9C:
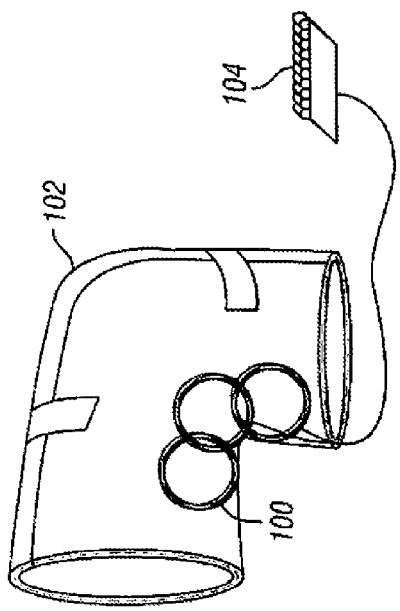
Figure 9D:
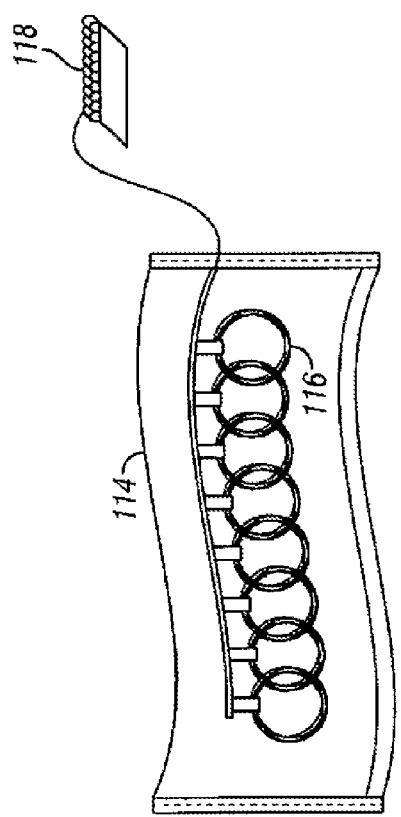

More particularly, FIG. 9A illustrates an embodiment, in which coils 100 are embedded in a knee wrap 102 and are connected to a logic controller (not shown) by a connector 104. FIG. 9B instead illustrates an embodiment, in which coils 106 are disposed within an abdominal garment, for example shorts 108 and in which coils 106 are also connected to a logic controller (not shown) by a connector 110. A marking 112 may be added on one side of shorts 108 to indicate wrap orientation. FIG. 9C illustrates a coil wrap shaped like a band 114, in which coils 116 are connected to a logic controller (not shown) by a connector 118. When this embodiment is employed, band 114 may be wrapped around a body portion (for example, an arm) and be retained in place by a system known in the art, for example, a hook and loop system, a strap and buckle system, or simply a hook disposed at one end of band 114 for engaging fabric or other material in another portion of band 114. FIG. 9D illustrates an embodiment shaped as a shoulder strap 120, the length of which may be adjusted by a buckle 122 and which has coils 124 disposed in one or more points, for example, at the joint between an arm and a shoulder as shown. Each of these embodiments includes one or ore sensors (not shown) that may coupled to the garment, or that may applied separately from the garment.

Other embodiments that are not illustrated include, bur are not limited to: a head worn garment, such as a cap; a neck worn garment, such as a neck brace; and a lower-back garment. Each garment and applicator may also utilize the locking, targeting coil feature described previously, without requiring the use of the any sensing components after a proper positioning of the coils in relation to the target nerve or nerves has been established.

Figure 10:
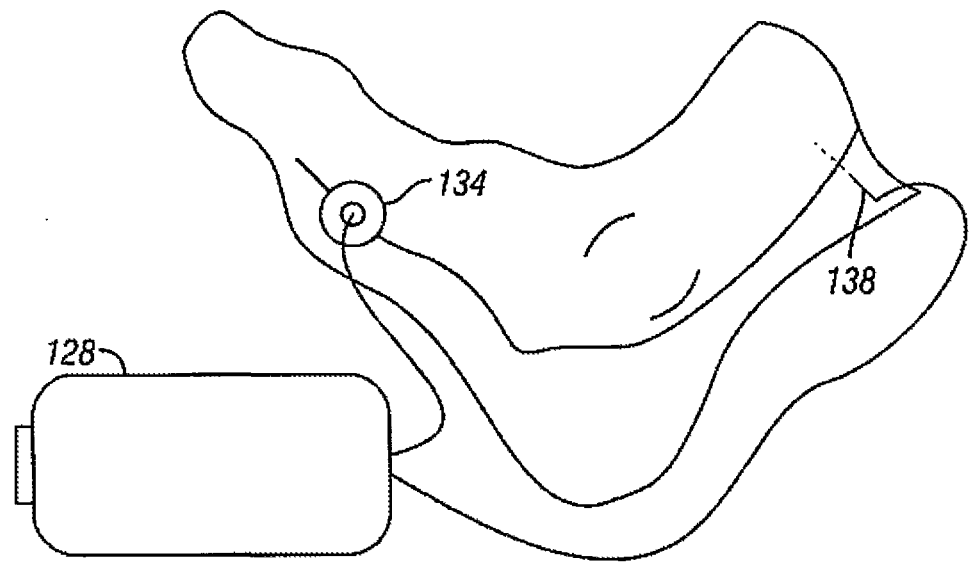
FIG. 10 shows a variation of a system including a percutaneous stimulator.
Figure 11:
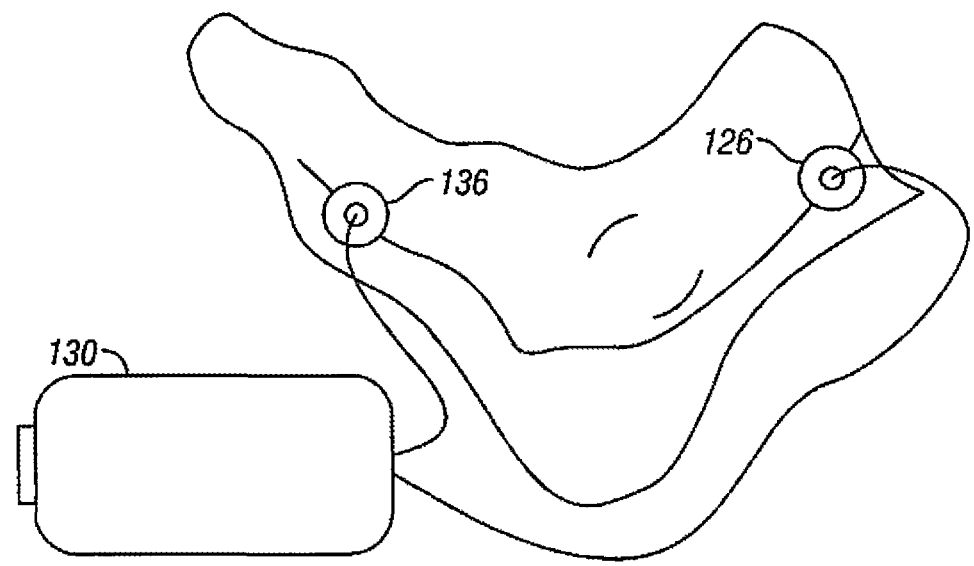
FIG. 11 shows a variation of a system including a transcutaneous stimulator.

Still other embodiments of the invention are depicted in FIGS. 10 and 11. In these embodiments, the source of energy for nerve stimulation is electrical energy that is dispensed through a percutaneous stimulator, such as a percutaneous needle 124, or a transcutaneous stimulator, such as an electrode 126. As shown in FIG. 10, an electrical pulse controller 128 is electrically connected both to percutaneous needle 124 and to sensor 134, to provide the desired feedback and modulate the power to percutaneous needle 134. In the embodiment of FIG. 11, electrical pulse controller 130 is connected both to electrode 126 and to sensor 136, and performs a function similar to that of electrical pulse controller 128. With these embodiments, nerve conduction may be detected at a site sufficiently distant from the site of stimulation, so to enable detection of nerve conduction despite the confounding interference from the direct electrical stimuli. Further, direct electrical stimulation of nerve and muscle may be tailored to provide optimal therapy and, in the case of electrode immigration or other electrode malfunction, to report lack of stimulation of the bodily tissues. Still further, these embodiments enable a reduction in power requirement, because control of the signal is provided by the sensor to the signal generator loop.

As shown, a device constructed according to the principles of the present invention provides a targeted and precise stimulation of the posterior tibial nerve, or of other peripheral nerves, in a non-invasive manner by employing an ergonomic wrap or cradle that specifically targets the posterior tibial nerve in a consistent and repeatable manner. For example, in patients with OAB or VI, the novel, reversibly lockable movement of the coils and the use of a logic controller-sensor loop enables the application of a magnetic field that can be varied in location, amplitude and strength according to the amount of stimulation actually induced in one or more target nerves and of the response of the patient to the therapy. An apparatus according to the present invention may deliver any frequency of stimulation, including low frequencies, high frequencies, mid frequencies and ultrahigh frequencies, and overlapping and non-overlapping coils may be used to generate the desired field, although overlapping or Helmholtz coils are preferred due to their ability to target a broader region and achieve more thorough stimulation.

Ailments that may be treated through the use of apparatus and methods of the present invention include not only OAB and VI, but also obesity, depression, urinary incontinence, fecal incontinence, hypertension, pain, back pain, restless leg syndrome, Guillain Barre syndrome, quadriplegia, paraplegia, diabetic polyneuropthy, dyskinesias, paresthesias, dental procedure pain, knee osteoarthritis, anesthesia (pain relief during surgery), Alzheimer's disease, angina (chest pain from heart disease), ankylosing spondylitis, back pain, burn pain, cancer pain, chronic pain, dysmenorrhea (painful menstruation), headache, hemiplegia, hemiparesis (paralysis on one side of the body), labor pain, local anesthesia during gallstone lithotripsy, facial pain, trigeminal neuralgia, bruxism (tooth grinding) pain, myofascial pain, pregnancy-related nausea or vomiting, neck and shoulder pain, pain from broken bones, rib fracture or acute trauma, diabetic peripheral neuropathy, phantom limb pain, post-herpetic neuralgia (pain after shingles), postoperative ileus (bowel obstruction), irritable bowel syndrome, postoperative nausea or vomiting, postoperative pain, post-stroke rehabilitation, rheumatoid arthritis, skin ulcers, spinal cord injury, temporomandibular joint pain, detrusor instability, spinal muscular atrophy (in children), pain during hysteroscopy, gastroparesis, chronic obstructive pulmonary disease rehabilitation, carpal tunnel syndrome, soft tissue injury, multiple sclerosis, intermittent claudication, attention-deficit hyperactivity disorder (ADHD), cognitive impairment, knee replacement pain, achalasia, atopic eczema, bursitis, carpal tunnel syndrome, dementia, depression, dry mouth, dystonia, enhanced blood flow in the brain, enhanced blood perfusion of the uterus and placenta, esophageal spasm, fibromyalgia, fracture pain, Guillain-Barre syndrome, hemophilia, herpes, hip pain, interstitial cystitis, irritable bowel syndrome, pruritis, joint pain, labor induction, local anesthesia, menstrual cramps, muscle cramps, muscle spasticity, muscle strain or pain, musculoskeletal trauma, myofascial pain dysfunction syndrome, nerve damage, osteoarthritis, pain medication adjunct, pancreatitis, Raynaud's phenomenon, repetitive strain injuries, sacral pain, schizophrenia, shingles, shoulder subluxation, sickle cell anemia pain, Skin flap ischemia (during plastic surgery), sphincter of Oddi disorders, sports injuries, thrombophlebitis, tinnitus (ringing in the ear), restless legs. tremor, whiplash and neuralgias. In contrast to implantable nerve stimulators, this therapy is completely non-invasive and does not require a major surgery to implant a permanent nerve stimulation device. Moreover, this therapy can be controlled to optimize the level of therapy delivered according to power consumption and nerve stimulation requirements and need not be delivered by a professional healthcare provider.

In other embodiments of the invention, neural stimulation may be applied as electrical transcutaneous stimulation, for example, by inserting an invasive electrical needle into a target body part and by modulating stimulation is modulated on the basis of information sent back to the logic controller from the one or more sensors that are used to detect and/or maintain the correct level of stimulation. The transcutaneous electrical stimulation sensor may be placed in the body independently or be incorporated within the wrap and may provide, among other things, feedback as to the quality of the electrical connection to the skin, which is directly related to the bum risk inherently associated with this type of therapy. In fact, these methods of stimulation may not be optimal due to the resulting skin irritation and risk of potential burns, a very serious issue in the large percentage of patients that have neuropathies. Even when patches are applied to monitor transcutaneous stimulation very closely, the patches may still become displaced and allow a burn to occur. Moreover, potentially interfering electrical impulses may develop at the treatment site, creating a noisy environment for the detection of nerve conduction.

In still other embodiments of the invention, an external coil or coils may be inductively connected to an implanted coil or coils may be utilized. In these embodiments, an ergonomic applicator may be adjusted by the user or by a healthcare provider such to optimize inductive power transmission between the external and implanted coils. One or more sensors may be utilized to provide a feedback that the relative coil positions have been optimized, and the external coil may then be reversibly locked into position within the ergonomic applicator. Two applications of this embodiment relate to the transfer of power to recharge an implantable device, and to the transfer of power to activate an implantable device.

In the first application, when an implantable rechargeable device is utilized, the external coils may be used for recharging the implanted device by means of inductive fields generated by the external coils. The external coils may include circuitry that determines the amount of resistance encountered by the magnetic field or other electrical properties related to the quality and degree of the magnetic coupling that is being established. Based on this feedback, the position of the external coils may be adjusted manually or automatically to optimize the coupling achieved with during each recharging session. Alternatively, a sensor may be incorporated into the implantable device and may communicate the degree and quality of the magnetic coupling to the external coils and/or the connected circuitry via wireless communication, providing a feedback for the automatic or manual adjustment of the external recharging coils.

The coils within the ergonomic applicator may be reversibly locked into place for the duration of the recharge session, and the implantable device may also communicate to the external recharging unit that the implantable device has been fully recharged, terminating the recharging session has been completed. By providing for an intermittent recharging of an implanted device, an apparatus according to the present invention enables the implantable device to devote more power to performing its intended function optimally and with a lesser concern about protecting or extending battery life.

In the second application, the powering coils may contain circuitry to determine the amount of resistance encountered by the applied magnetic field, or other electrical properties that may reflect the quality and degree of the magnetic coupling that is being achieved. Based on this feedback, the powering coils in the applicator may be adjusted manually or automatically to activate and optimize the coil coupling at the beginning of each therapy session. Alternatively, a sensor may be incorporated into the implantable device and communicate the degree and quality of the magnetic coupling externally via wireless communication, which may in turn provide feedback for the automatic or manual adjustment of the powering coil. In one variant of the present embodiment, the inductive coils may be magnetically coupled to a needle targeting the posterior tibial nerve.

An exemplary method of use of an apparatus according to the present invention on a patient suffering from VI and/or OAB includes the following steps:

The patient places a conductive wrap contained within a flexible material over a region of the ankle (or alternatively over the knee) to provide the required pulsed magnetic field. Alternatively, the patient may use an ergonomic foot/leg rest or cradle having embedded coils.

A sensor (for example, a sensor patch) is placed on the patient's body along the path of the nerve, ideally proximal to the stimulation site to ensure afferent nerve stimulation, and is connected to a logic controller.

A physician or healthcare provider adjusts the coils in the wrap or cradle until nerve conduction is achieved based on patient and sensor feedback. An optimal position is sought, and the coils may be reversibly locked into position within the conductive wrap or ergonomic cradle and remain in this position during subsequent use.

During the therapy session, the. logic controller provides an electric current to the coils, generating an inductive magnetic field. In one embodiment, this field begins at low amplitude and slowly ramps up until nerve conduction exceeds a threshold level, as signaled by the sensor and possibly by the patient, who may feel motory conduction. Alternatively, one or more coils may also be activated to increase the covered area of stimulation in the event that stimulation does not occur with the initial coil configuration or is inadequate The optimal stimulation may be determined in a variety of manners, for example, by measuring exposure to electromagnetic fields capable of generating a square wave electric signal at a frequency of 10-30 Hz at the targeted tissue depth. The square wave configuration of the signal may be generated via Fourier transformation or may be a ramped current generated in any manner.

The inductive magnetic pulses continue for an appropriate duration of use, for example, for 15-30 minutes. The sensor may remain in place during the entire therapy session to ensure that stimulation occurs consistently and to provide for appropriate corrections if nerve conduction deteriorated. The logic controller may be powered either by a portable power source such as a battery, or by or a fixed power source such as a traditional wall outlet.

The conductive wrap and/or ergonomic cradle is removed from the body when therapeutic stimulation is not being delivered, typically at the end of the therapy session.

The conductive wrap and/or ergonomic cradle is reapplied along with the sensor patch (ideally disposable) from time to time as indicated, for example, on a daily basis, and steps 4-8 are repeated.

The invention described herein may be applied to any body tissues, including nerve, muscle, skin, vasculature, or any other organ or tissue within the human body. Further, the devices and methods described herein may be used to treat any conditions suited for neuromodulation regardless of whether the stimulation source is an electromagnetic field, a direct electric current, a RF field, infrared energy, visible light, ultraviolet light, ultrasound, or other energy dispensing device.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. A method of controlling magnetic induction therapy in the treatment of overactive bladder, comprising:
    positioning a first portion of a patient's body relative to a housing such that a posterior tibial nerve within the first portion of the body is in proximity to at least one conductive coil disposed within or along the housing wherein the housing is positioned external to the patient;
    increasing a current through the at least one coil to generate a magnetic field and to deliver the magnetic field to the posterior tibial nerve until conduction through the nerve is detected wherein the magnetic field stimulates the posterior tibial nerve; and
    adjusting the current via a controller in communication with the at least one conductive coil based on the detected conduction to control the therapy for treating overactive bladder.

2. The method of claim 1 wherein positioning a first portion of a patient's body comprises placing an ankle leg relative to the housing.

3. The method of claim 1 wherein increasing a current comprises passing the current through a plurality of coils to generate the magnetic field.

4. The method of claim 1 wherein increasing a current further comprises detecting the conduction through the nerve along a second portion of the body in proximity to the nerve.

5. The method of claim 1 wherein the conduction is detected through the nerve by the patient.

6. The method of claim 1 wherein adjusting the current via the controller comprises actuating a patient-operated control to adjust the current through the at least one coil.

7. The method of claim 1, wherein current is increased through the at least one coil to generate a magnetic field focused on the nerve until a signal indicating that an afferent nerve of the nerve has been stimulated is detected.

8. A method of controlling magnetic induction therapy in the treatment of overactive bladder, comprising:
    positioning a first portion of a patient's body relative to a housing such that a posterior tibial nerve within the first portion of the body is in proximity to at least one conductive coil disposed within or along the housing wherein the housing is positioned external to the patient;
    increasing a current through the at least one coil to generate a magnetic field and to deliver the magnetic field to the posterior tibial nerve until conduction through the nerve is detected by the patient wherein the magnetic field stimulates the posterior tibial nerve; and
    actuating a patient-operated controller in communication with the at least one conductive coil to adjust the current based on the detected conduction to control the therapy for treating overactive bladder.

9. The method of claim 8 wherein positioning a first portion of a patient's body comprises placing an ankle relative to the housing.

10. The method of claim 8 wherein increasing a current comprises passing the current through a plurality of coils to generate the magnetic field.

11. The method of claim 8 wherein increasing a current comprises further detecting conduction through the nerve via at least one sensor in proximity to the nerve and which is in communication with the controller.

12. The method of claim 8 wherein increasing a current comprises increasing the current until paresthesia is detected by the patient.

13. The method of claim 12 wherein actuating a patient-operated controller comprises having the patient reduce the current until the paresthesia is undetectable by the patient.

14. The method of claim 13 further comprising maintaining the current for a predetermined period of time.

15. The method of claim 8, wherein current is increased through the at least one coil to generate a magnetic field focused on the nerve until a signal indicating that an afferent nerve of the nerve has been stimulated is detected.

* * * * *